US012582316B2

(12) United States Patent
Trakic et al.

(10) Patent No.: US 12,582,316 B2
(45) Date of Patent: Mar. 24, 2026

(54) APPARATUS AND PROCESS FOR ELECTROMAGNETIC IMAGING

(71) Applicant: EMvision Medical Devices Ltd, Brisbane (AU)

(72) Inventors: Adnan Trakic, Brisbane (AU); Aida Brankovic, Brisbane (AU); Amin Abbosh, Brisbane (AU)

(73) Assignee: EMvision Medical Devices Ltd, Brisbane (AU)

( * ) Notice: Subject to any disclaimer, the term of this patent is extended or adjusted under 35 U.S.C. 154(b) by 689 days.

(21) Appl. No.: 17/634,211

(22) PCT Filed: Aug. 7, 2020

(86) PCT No.: PCT/AU2020/050819
§ 371 (c)(1),
(2) Date: Feb. 9, 2022

(87) PCT Pub. No.: WO2021/026592
PCT Pub. Date: Feb. 18, 2021

(65) Prior Publication Data
US 2022/0322940 A1 Oct. 13, 2022

(30) Foreign Application Priority Data

Aug. 9, 2019 (AU) ................................ 2019902867

(51) Int. Cl.
A61B 5/00 (2006.01)
A61B 5/05 (2021.01)
G01N 22/00 (2006.01)

(52) U.S. Cl.
CPC .............. *A61B 5/0042* (2013.01); *A61B 5/05* (2013.01); *A61B 5/4064* (2013.01); (Continued)

(58) Field of Classification Search
CPC ....... A61B 5/0042; A61B 5/05; A61B 5/4064; A61B 5/6814; A61B 5/7264
See application file for complete search history.

(56) References Cited

U.S. PATENT DOCUMENTS

2013/0303901 A1 11/2013 Afsar et al.

FOREIGN PATENT DOCUMENTS

WO WO 2007/105963 A1 9/2007
WO WO-2018098387 A1 * 5/2018 ........... A61B 5/0042
WO WO-2018115858 A1 * 6/2018 ........... A61B 5/0507

OTHER PUBLICATIONS

Written Opinion of the International Searching Authority, PCT/AU2020/050819, dated Sep. 11, 2020, in 10 pages.
(Continued)

*Primary Examiner* — David E Smith
(74) *Attorney, Agent, or Firm* — KNOBBE, MARTENS, OLSON & BEAR, LLP

(57) ABSTRACT

A computer-implemented process for electromagnetic imaging, the process including the steps of: accessing scattering data representing at least a two-dimensional array of measurements of electromagnetic wave scattering by internal features of an object, wherein each said measurement represents scattering of electromagnetic waves emitted by a corresponding antenna of an array of antennas disposed about the object as measured by a corresponding antenna of the array of antennas; and processing the scattering data to generate image data representing a spatial distribution of internal features of the object, wherein the generation of the image data does not involve tomographic reconstruction but is in accordance with a weighted mapping to directly map the measurements of electromagnetic wave scattering to a corresponding spatial distribution of electromagnetic wave scattering by the internal features of the object that corresponds to the physical shape of the object to enable the (Continued)

(a)

(b)

(c)

detection, localization, size estimation, shape estimation and classification of one or more features of interest of the object.

40 Claims, 26 Drawing Sheets

(52) U.S. Cl.
   CPC .......... *A61B 5/6814* (2013.01); *A61B 5/7264* (2013.01); *A61B 2562/046* (2013.01); *A61B 2576/026* (2013.01); *G01N 22/00* (2013.01)

(56) References Cited

OTHER PUBLICATIONS

Trakic et al., "Expedited Stroke Imaging with Electromagnetic Polar Sensitivity Encoding," IEEE Transactions on Antennas and Propagation, published May 29, 2020, (early access article) [retrieved from internet Sep. 9, 2020] <URL:https://ieeexplore.ieee.org/document/9103981><doi: 10.1109/TAP.2020.2996810>FIG. 1 and 6, sections "II. Mehtods" and "III. Results".

* cited by examiner (d)
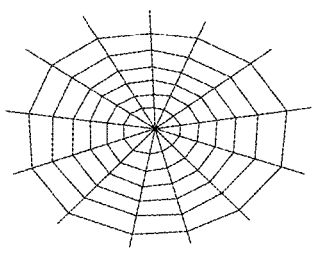
(h)
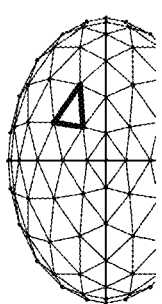
(c)
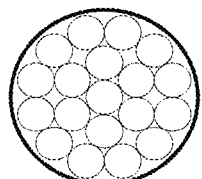
(g)
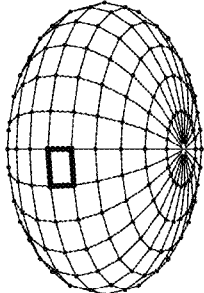
(b)
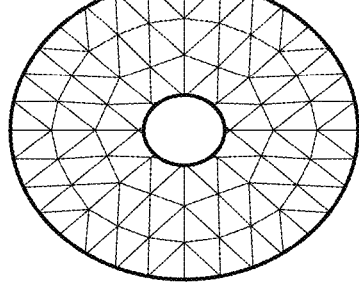
(f)
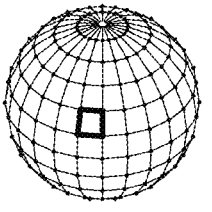
(a)
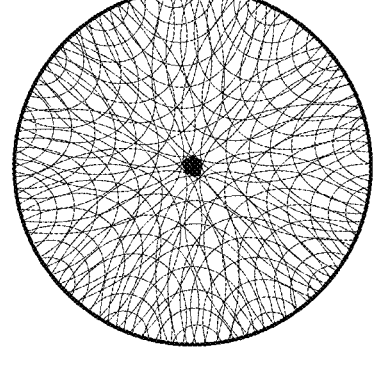
(e)
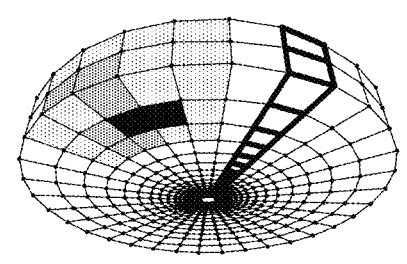
FIGURE 1

Stroke detected at antenna 3
and near the edge of the head

Stroke detected in the centre

Large stroke detected at
the back for the head

Stroke near antenna 10          Stroke near antenna 4
Raw data (magnitude)                Raw data (magnitude)
(a)
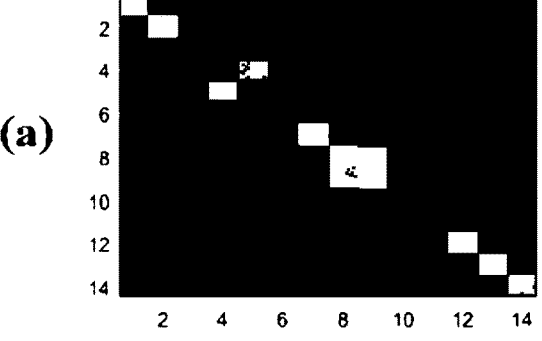
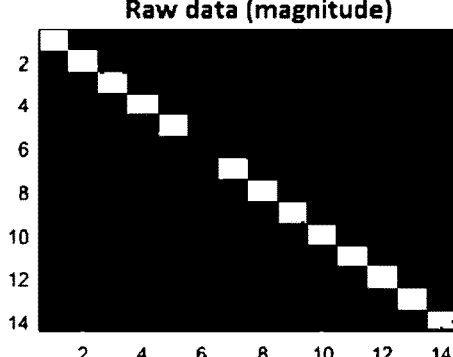
Background reference (magnitude)    Background reference (magnitude)
(b)
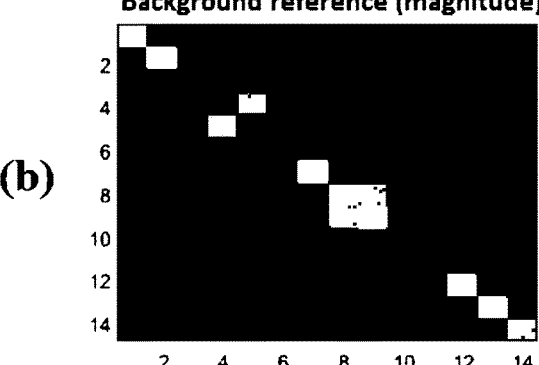
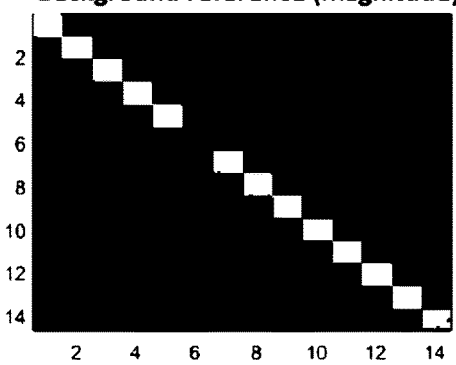
Raw data - reference (magnitude)   Raw data - reference (magnitude)
(c)
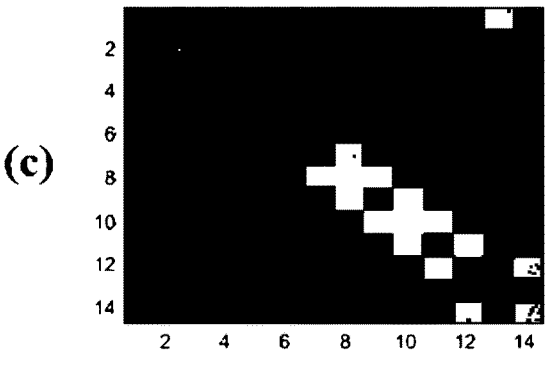
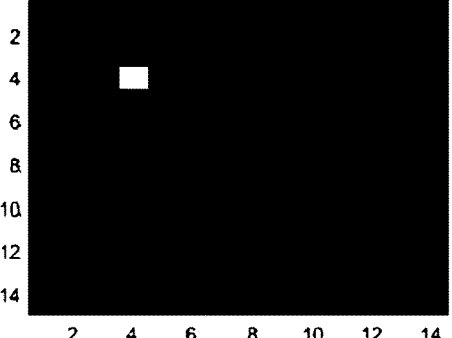
Decomposition $|V^T D + D^T V|$     Decomposition $|V^T D + D^T V|$
(d)
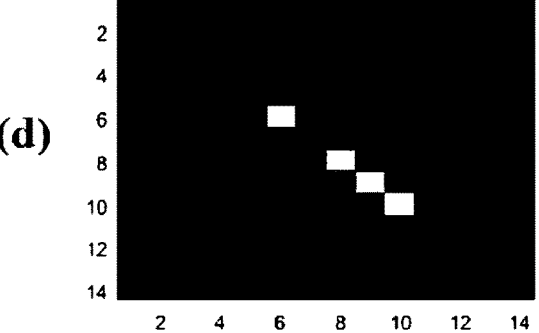
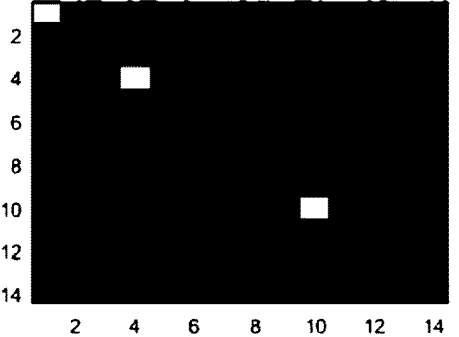
FIGURE 13

BLEEDING

CLOT

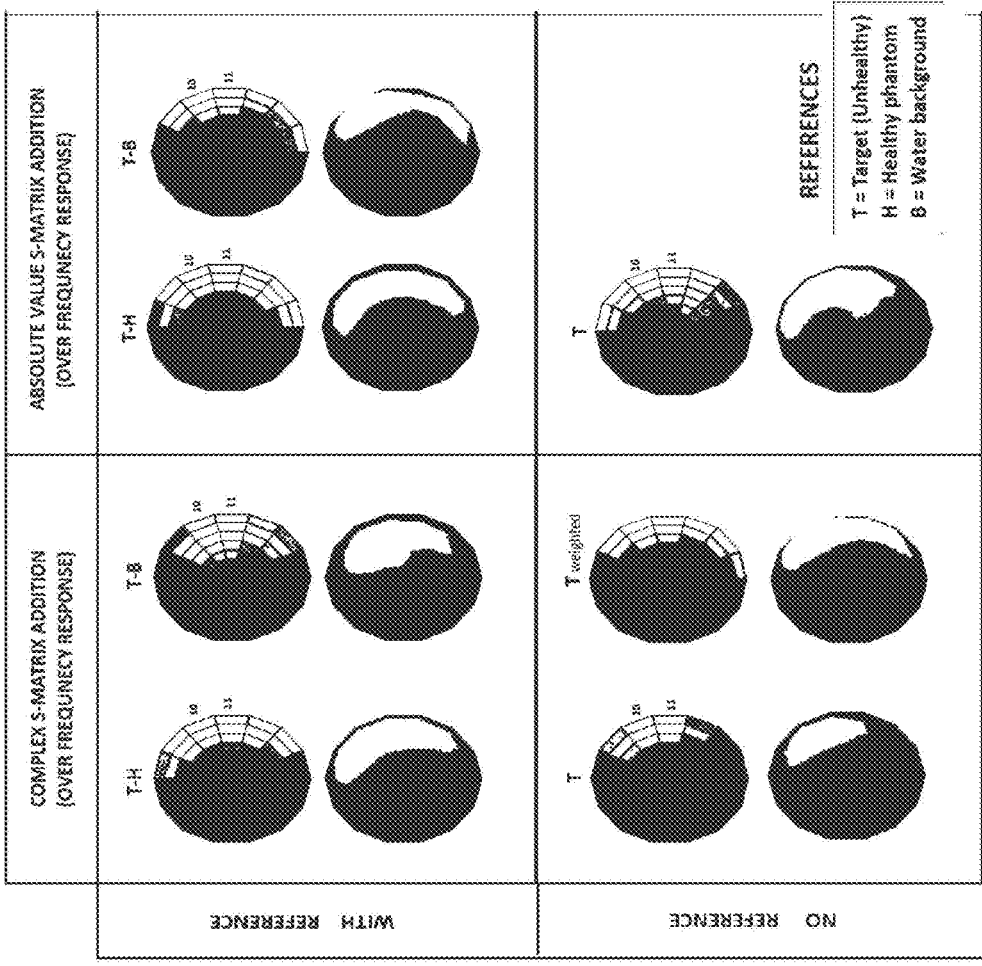
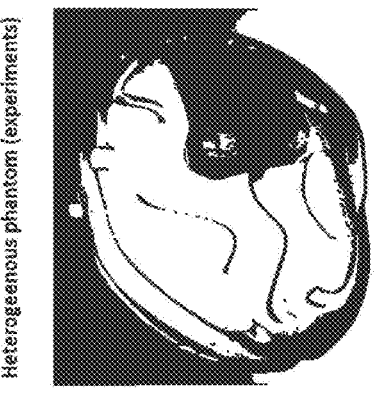
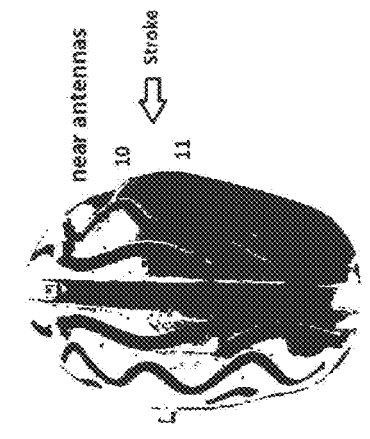
FIGURE 17

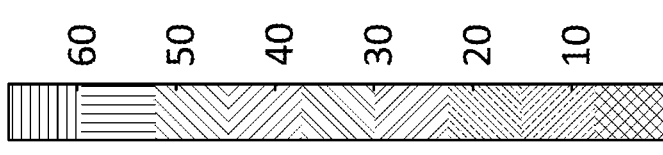
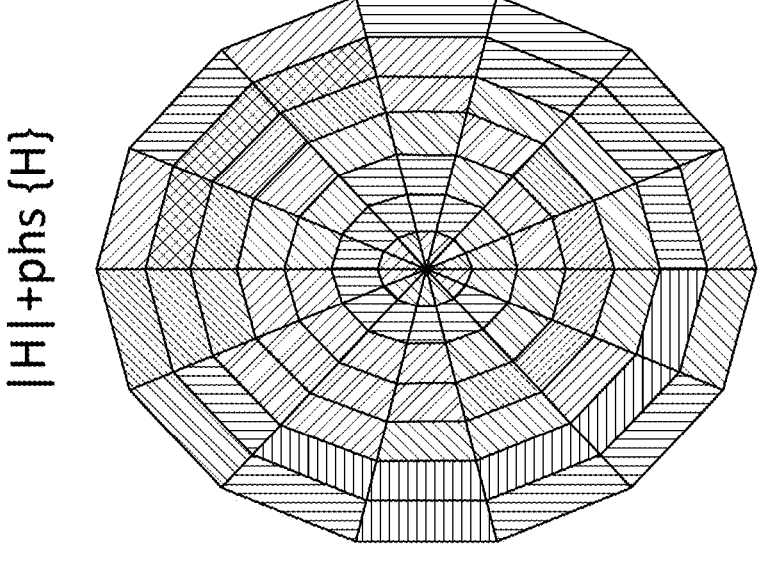
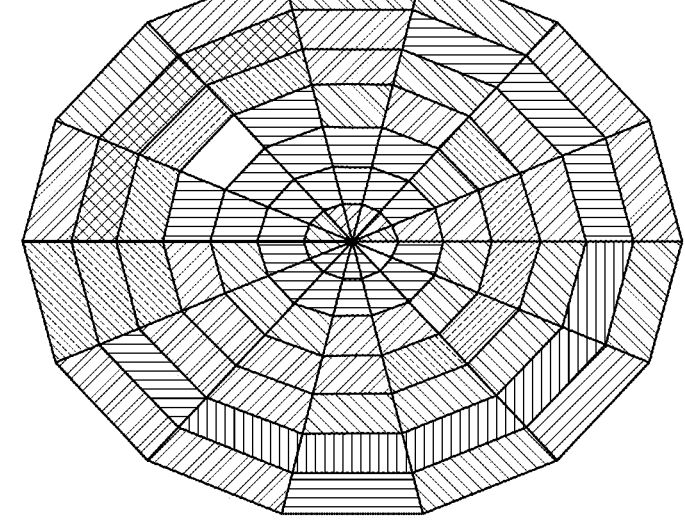
FIGURE 18

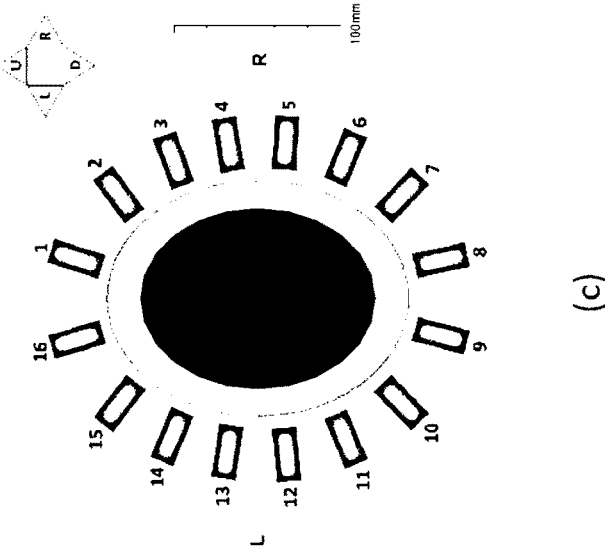
(c)
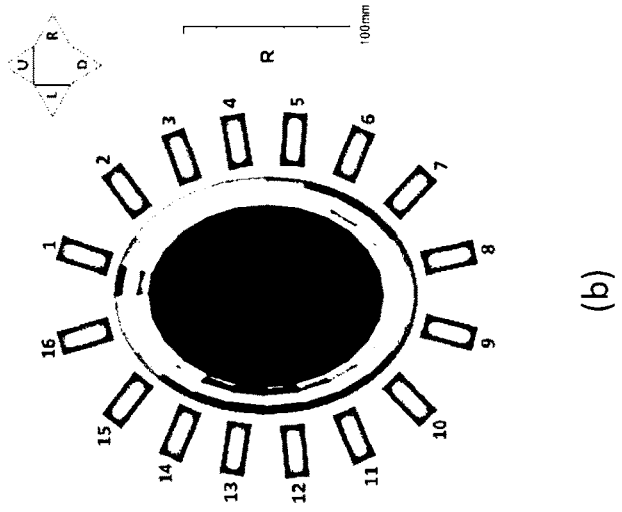
(b)
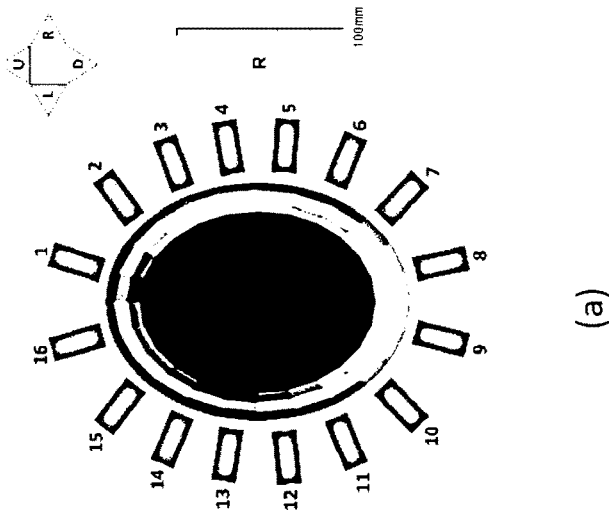
(a)
FIGURE 19

antenna finite
element
- like grid

(c)

magnitude stroke

(b)

Finite
element
surface

Finite
element
node

Intensity min          ⇧          max
          value

● Example node where $S_{3,13}$ , $S_{6,14}$ and $S_{8,15}$ intersect

● Example node where $S_{3,13}$ and $S_{9,16}$ intersect

○ Example node where $S_{4,14}$ and $S_{8,15}$ intersect

○ Example node where $S_{4,14}$ , $S_{7,15}$ and $S_{9,16}$ intersect

Example of finite element intensity value calculation $$Intensity = \frac{\{2 \times (S_{3,13} + S_{8,15} + S_{4,14}) + S_{9,16} + S_{7,15}\}}{4}$$

(d)          (e)          (f)

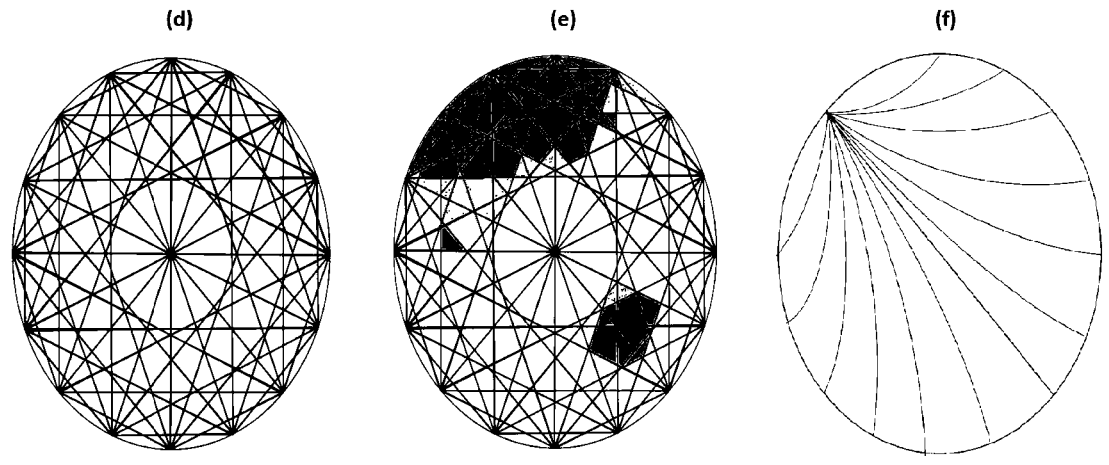

FIGURE 23

Patient
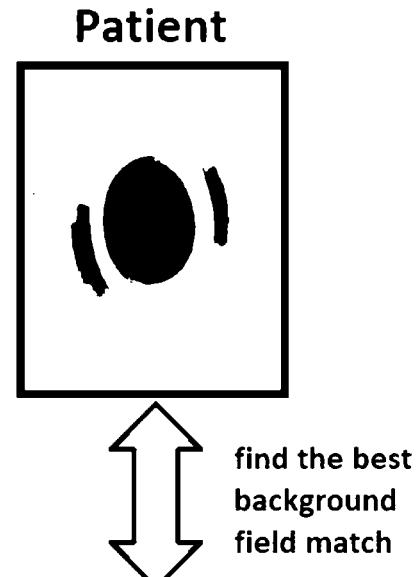
find the best
background
field match
HVR database
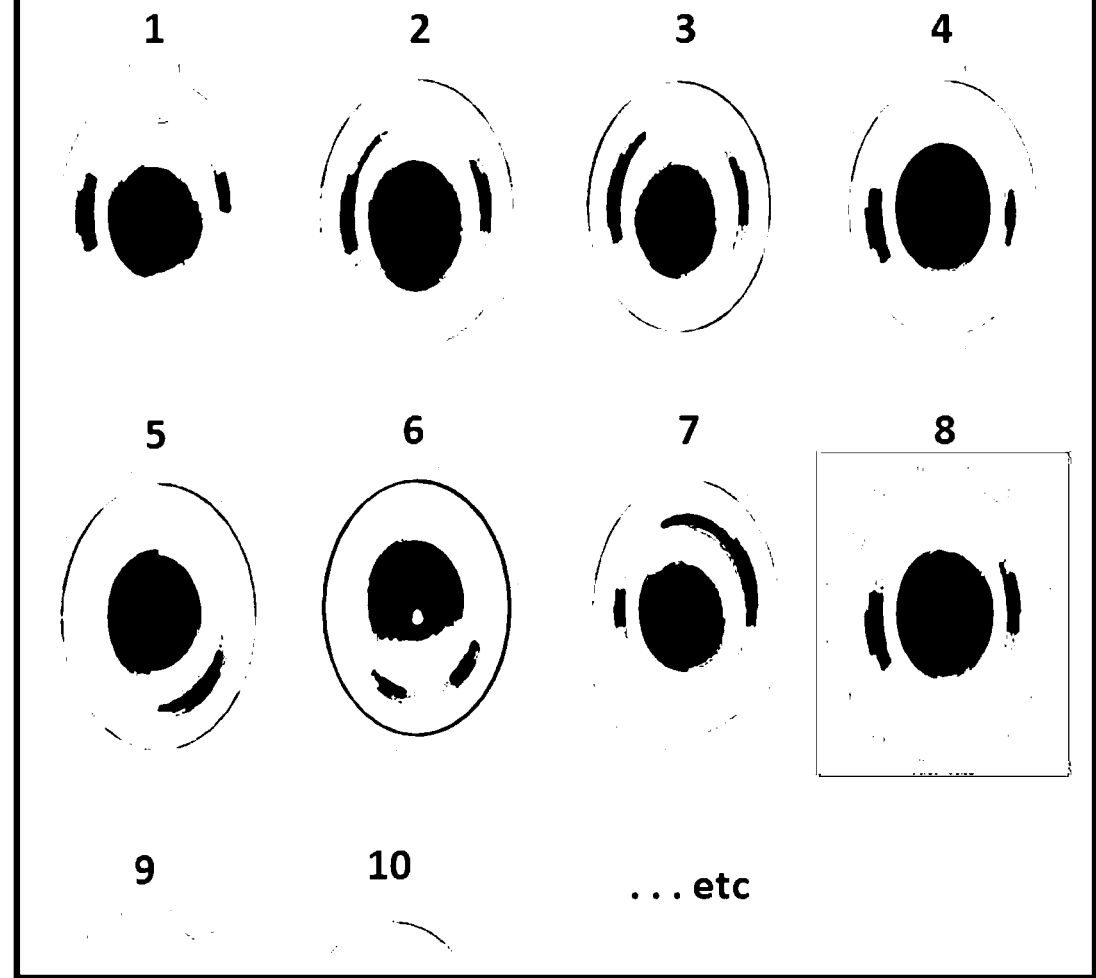
FIGURE 24

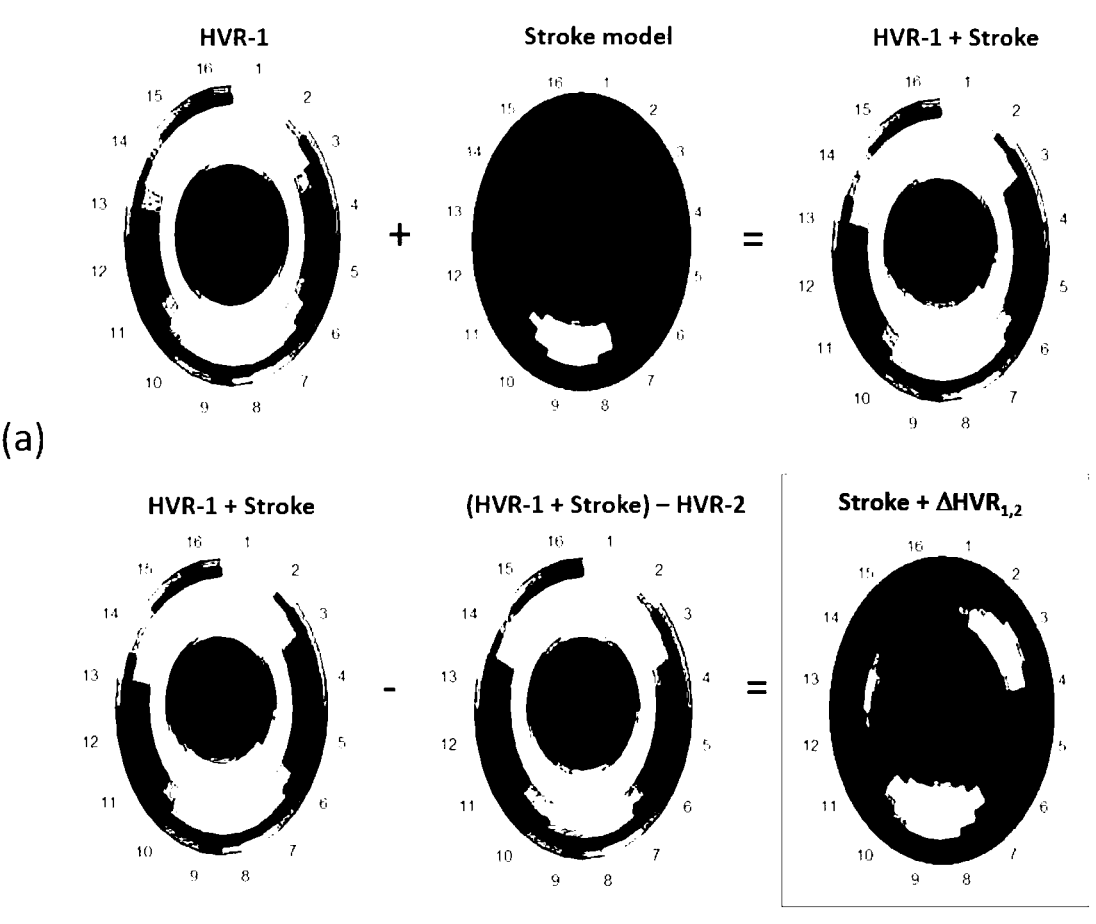
(a)
Same scale used (i.e. not normalized)
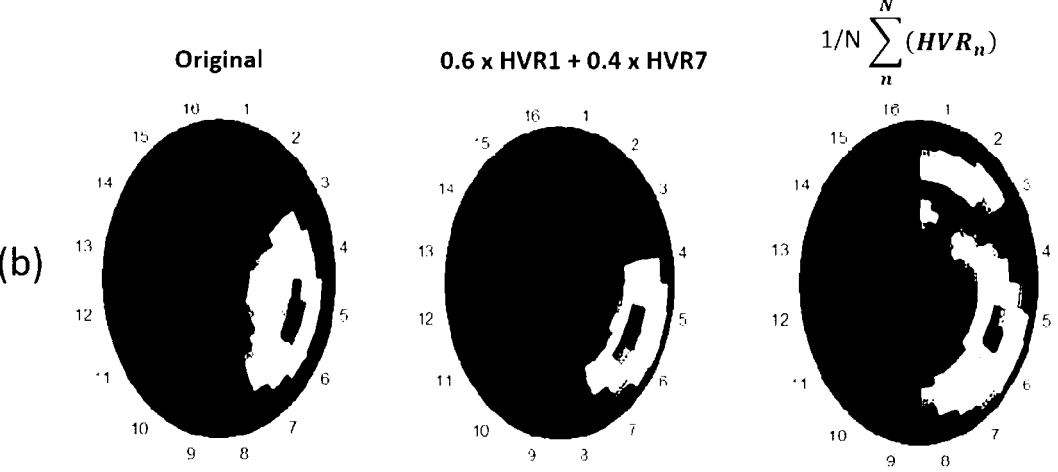
(b)
FIGURE 25

APPARATUS AND PROCESS FOR ELECTROMAGNETIC IMAGING

TECHNICAL FIELD

The present invention relates to electromagnetic imaging, and in particular to an apparatus and computer-implemented process for electromagnetic imaging of internal features of an object, such as may be used to detect, image and characterize abnormal tissues such as stroke and tumors in a body part such as a patient's head, for example.

BACKGROUND

The reference in this specification to any prior publication (or information derived from it), or to any matter which is known, is not, and should not be taken as an acknowledgment or admission or any form of suggestion that that prior publication (or information derived from it) or known matter forms part of the common general knowledge in the field of endeavour to which this specification relates.

Whilst magnetic resonance imaging (MRI) and computed tomography (CT) are gold standard medical imaging modalities, they are very expensive, limited in number for a given community, bulky and non-portable for emergency situations, and take a very long time (typically up to about 40 min) to prepare and scan the patient. Accordingly, electromagnetic based imaging, localization and classification of stroke and other pathologies has been widely studied in the literature as a much more affordable, readily available and portable imaging alternative. Low-power electromagnetic based imaging (at frequencies from 100 MHz and typically up to no more than 4 GHz) is of particular interest because the shorter wavelength electromagnetic fields can penetrate further into the human head and produce images with higher spatial resolution than electromagnetic fields with frequencies below 100 MHz.

Research studies are performed utilizing antenna arrays, wherein each antenna has a corresponding dedicated and independent electronic transmit-receive channel to enable the collection of an entire matrix of measured scattering parameters, typically but not always being S-parameters or Z-parameters. For example, for each frequency point in a spectrum of frequencies, the $S_{ii}$ and $S_{ij}$-parameters can be directly collected by a vector network analyzer and stored as a 2-dimensional N×N matrix, where N is the number of channels and antennas in the array. In the remainder of this specification, S-parameter measurements are used as representative examples of scattering parameters, although it should be understood that other types of electromagnetic scattering measurements known to those skilled in the art, such as Z-parameters for example, can be used instead of or in addition to S-parameters.

The antennas can be wide and varied in configuration and style, for instance often taking the form of dielectrically loaded waveguides or patch antennas. The size of the antennas determines both the number of antennas that can be fitted around the head or other body part, as well as the frequency bandwidth over which the antennas are able to operate. For example in the case of the human head imaging, typically the antennas are arranged circumferentially around the head, with each pointing towards the head. Normally, a coupling medium is inserted between the antenna aperture and the head surface in order to reduce the impedance mismatch and power reflection.

Ideally, S-parameter N×N matrix measurements are first performed with the target pathology (such as stroke), and then the measurements are repeated with a background reference that does not contain the target pathology. This background reference can, for example, involve any one or combination of the following: (i) an empty space background reference, (ii) a homogeneous reference such as a water bath, (iii) a dedicated phantom that fills the space within the array, (iv) a dedicated homogenous or inhomogeneous phantom that takes the shape of the head, and/or (v) a digital phantom that is derived from a set of magnetic resonance imaging (MRI) or computed tomography (CT) scans of the patient in combination with an electromagnetic field solver (software based) that is able to accurately emulate the experimental measurement. Although the reference scan is absolutely not necessary, in many cases it can help substantially to improve the target stroke (or pathology) signal differentiation and therefore the detection, localization and classification of the same (by subtraction, i.e. $\Delta S$).

In the case of stroke disease, strokes typically occur in one of two types: (i) hemorrhagic or (ii) ischemic. A hemorrhagic stroke is a type of stroke wherein a blood vessel has ruptured, causing uncontrollable bleeding into normal tissue regions, often resulting in substantial intracranial pressure, and leading to partial/complete disability, coma, or death. Similarly dangerous is the ischemic stroke, wherein a small (blood) clot has blocked blood flow to a certain part of the brain. This type of stroke is typically below the spatial resolution of microwave imaging, and is usually not immediately visible and differentiable from normal tissue, even on MRI and CT scans. However, over several hours or days, as a water-based edema forms around the clot occlusion, an ischemic stroke becomes readily detected using microwave imaging technology. The electromagnetic dielectric properties (electrical conductivity and relative permittivity) of an ischemic stroke are known to be approximately 5-20% lower than the head-average dielectric properties of healthy tissue, and consequently provide a somewhat lower microwave imaging contrast in respect to the neighboring healthy tissue, as opposed to a hemorrhagic stroke, which has higher dielectric properties than head-average healthy tissue and therefore yields higher image contrast.

To image such diseases using electromagnetic medical imaging, tomographic imaging methods are used, relying on electromagnetic field solvers based on Maxwell's field equations or variants of the same implemented on a high-speed computer. For any tomographic method to be usable for medical imaging, it is critical to ensure that these solvers can routinely match real-world electromagnetic field-tissue interactions. These electromagnetic field solvers are often called 'forward' or 'inverse' solvers, and are used in conjunction with the S-parameter measurements as part of the objective function to iteratively optimize a calculated electromagnetic field so that it matches that of the real-world case. There are vast numbers of such algorithms, which are often based on local/global integral or differential tomographic models, often containing Born iterative solvers. Normally the outputs of such optimizations are spatial maps of electrical conductivity and relative permittivity of tissue, often (roughly) indicating the distribution of dielectric properties of the target (i.e., abnormal) tissue, which may or may not be easily visible and differentiated from the surrounding dielectric distribution of normal tissue. In addition, tomographic methods need to solve for orders of magnitude larger number of unknowns than the number of known measurements (e.g., such as for example 10,000 unknowns in a 100×100 2D tomographic image, whereas the number of measurements is for example only 169 given an array of 14 antennas). Incidentally, tomographic methods suffer from the real possibility that the final imaging result may not converge despite using the best optimization solvers.

Another common characteristic of the tomographic methods mentioned above is a typically long computational time, even with 2D assumptions (i.e., the subject's anatomy is assumed to be invariant with respect to the z-direction as the third spatial dimension). For example, the computations usually require a wall clock time of several minutes at a minimum, and even hours in cases requiring a high isotropic image spatial resolution (such as 1 mm or 2 mm for example) to ensure accuracy. Accordingly, a 3D tomographic modelling system may be practically infeasible because the number of voxels increases as the third power of the spatial resolution, and the number of additional electromagnetic tensor field components increases three-fold to a maximum of nine. This would then require substantial investments in supercomputing power (both in terms of the number of CPUs and the amount of RAM), and any tomographic techniques based on, for example, the method of moments (MoM), finite difference time domain (FDTD) or finite element methods (FEM) would require sophisticated parallel computing algorithms, which may not necessarily provide the desired/required computation acceleration (especially for emergency case situations of stroke, for instance), despite the large computing resource investment.

Furthermore, radar-based imaging methods require a reasonably accurate dielectric (digital) tissue template of the patient, which is typically unknown due to the large anatomical inter-patient variability, and is not readily available without additional use of MRI or CT to provide the required morphology for segmentation and digitization.

It is desired, therefore, to provide and apparatus and computer-implemented process for electromagnetic imaging that overcome or alleviate one or more difficulties of the prior art, or to at least provide a useful alternative.

SUMMARY

In accordance with the present invention, there is provided a computer-implemented process for electromagnetic imaging, the process including the steps of:

accessing scattering data representing at least a two-dimensional array of measurements of electromagnetic wave scattering by internal features of an object, wherein each said measurement represents scattering of electromagnetic waves emitted by a corresponding antenna of an array of antennas disposed about the object as measured by a corresponding antenna of the array of antennas; and processing the scattering data to generate image data representing a spatial distribution of internal features of the object, wherein the generation of the image data does not involve tomographic reconstruction but is in accordance with a weighted mapping to directly map the measurements of electromagnetic wave scattering to a corresponding spatial distribution of electromagnetic wave scattering by the internal features of the object that corresponds to the physical shape of the object to enable the detection, localization, size estimation, shape estimation and classification of one or more features of interest of the object.

In some embodiments, the weighted mapping includes calculating weighting coefficients from at least one ground truth, and applying the weighting coefficients to the scattering data. In other embodiments, the weighted mapping corresponds to a spatial distribution of electromagnetic radiation emission from each said antenna.

4

In some embodiments, the object has a curved physical shape, and the spatial distribution of electromagnetic wave scattering is generated using a non-Cartesian coordinate system that better conforms to the physical shape of the object than a corresponding Cartesian coordinate system.

In some embodiments, the measurements include S-parameter reflection coefficients and/or Z-impedance coefficients.

In some embodiments, the spatial distribution of electromagnetic wave scattering is represented by at least one of the following:
(a) a polar grid;
(b) an elliptical grid;
(c) a triangular finite-element type grid;
(d) a multi-gonal grid;
(e) an anatomical template with a dedicated anatomically conformal grid;
(f) a cylindrical grid;
(g) a spherical grid;
(h) an ellipsoidal/spheroidal grid; and
(i) a finite element grid (tetrahedral or multi-hedral).

In some embodiments, the process includes generating the measurements of electromagnetic wave scattering by subtracting respective background/reference measurements of electromagnetic wave scattering from respective raw measurements of electromagnetic wave scattering by the internal features of the body part, wherein the background/reference measurements are selected from:
(a) a homogeneous background reference;
(b) a background reference with dielectric properties that spatially vary according to a known function;
(c) a virtual/digital anatomical template/reference;
(d) a reference based on symmetry of the object; and
(e) a healthy human reference, or a weighted combination of healthy human references.

In some embodiments, the process includes the steps of:
accessing raw scattering data representing a two-dimensional array of raw measurements of electromagnetic wave scattering by internal features of the object, wherein each said raw measurement represents scattering of electromagnetic waves emitted by a corresponding antenna of an array of antennas disposed about the object as measured by the corresponding antenna of the array of antennas; and
performing matrix decomposition of the two-dimensional array of raw measurements to extract localization information on the internal features of the object, using at least one of the following matrix decomposition methods:
(a) eigenvalue/eigenvector decomposition;
(b) Schur decomposition; and
(c) singular value decomposition.

In some embodiments, the process includes the steps of:
selecting a frequency for mapping that corresponds to one of:
(a) maximum and/or minimum (magnitude) value of the average ii-diagonal S-parameter frequency response data;
(b) a peak (magnitude) value of a Z-impedance frequency response; and/or
(c) an absolute-value or complex-value S-parameter integration, or an integration of a mathematical S-parameter expression, over a select frequency band of interest.

In some embodiments, the process includes generating an output image in polar space, following the Cartesian parameters to polar space mapping, by at least one of the following:

(a) for each antenna in the array, by summing intensity values from azimuthal cells from each polar ring to yield a single intensity value that is assigned to the polar cell with coordinates (r-index, φ-index), wherein the φ-index is an antenna number in the array; and (b) the resulting intensity distributions for each antenna in the array are summed over the overlapping cell regions.

In some embodiments, the process includes the step of classifying an abnormal tissue type as a clot or a hemorrhage based on comparison of a statistical mean, standard deviation and/or variance of one or more of magnitude and phase of the scattering data with one or more corresponding threshold values.

In some embodiments, absolute phase values of the scattering data are used in the direct mapping to generate the corresponding spatial distribution of electromagnetic wave scattering by the internal features of the object.

In some embodiments, the process includes combining complex values, absolute values or real/imaginary values of S-parameter matrices for different frequencies to generate a corresponding S-matrix for the direct mapping.

In some embodiments, the scattering data represents a three-dimensional array of measurements of electromagnetic wave scattering by internal features of an object, wherein each said measurement represents scattering of electromagnetic waves emitted by a corresponding antenna of a three-dimensional array of antennas disposed about the object as measured by a corresponding antenna of the array of antennas, and the scattering data includes a dimension representing frequency response.

In some embodiments, one or more antennas of the array of antennas was or were moved during acquisition of the scattering data, and the scattering data includes a dimension representing frequency response, and a dimension representing corresponding positions of the one or more antennas during the acquisition.

In some embodiments, the spatial distribution is represented on a mesh defined by lines interconnecting the positions of each and every antenna in the array to create nodes of the mesh where the lines intersect, and surfaces of the mesh where the lines define polygonal elements.

In some embodiments, the process includes assigning a colour to each surface of the mesh corresponding to an intensity value calculated as a weighted sum of complex Sij-parameters that correspond to each line of the mesh.

In some embodiments, the spatial distribution is represented on a mesh defined by iso-contour lines representing a near-field electromagnetic field distribution.

In some embodiments, the object is a body part, the internal features are internal tissues of the body part, and the one or more features of interest are abnormal tissues of the body part.

In some embodiments, the body part includes a brain, and the abnormal tissues include one or more stroke regions of the brain.

In some embodiments, the spatial distribution is represented on a mesh having an elliptical shape or a shape corresponding to a human head.

In some embodiments, the object is a body part, and the process includes the steps of localising and classifying an abnormal tissue of the body part.

In some embodiments, the object is a body part of a subject, and the process includes the steps of classifying the subject as either 'healthy' or 'unhealthy', and if unhealthy, then classifying a corresponding pathology of the subject as being one of a plurality of predetermined pathology types.

In some embodiments, the object is a body part, and the electromagnetic wave scattering includes scattering of electromagnetic waves of relatively lower frequency to provide more robust localization and pathology side indication in body symmetric systems, and scattering of electromagnetic waves of higher frequency to improve spatial resolution and size and shape estimation of the pathology.

In some embodiments, the object is a body part, and the process includes determining a location of the body part relative to a geometric center of the array of antennas disposed about the body part.

In some embodiments, the process includes processing the determined location to compensate for artefacts resulting from the location of the body part being offset from the geometric center of the array of antennas.

In some embodiments, the body part offset compensation is accomplished by selecting an offset background reference from a database, and applying the selected offset background reference to generate a corresponding target pathology image.

In some embodiments, the process includes weighting a scattering intensity distribution by the quantified body offset in order to compensate for imaging artefacts introduced by the body offset.

In some embodiments, the process includes displaying offsets of the body part from the geometric center of the array of antennas substantially in real-time in order to facilitate centering of the body part relative to the array of antennas immediately prior to measuring the electromagnetic wave scattering, in order to reduce image artefacts.

In some embodiments, the location of the body part is determined without the use of any external reference.

In some embodiments, the process includes displaying a direction and amount of offset of the object relative to the geometric center of the array of antennas.

In some embodiments, the process includes searching a database of measurements of healthy subjects to select a set of measurements of a healthy subject or a set of combined measurements of multiple healthy subjects that is similar to the measurements of a patient, and using the selected set as a reference to reduce a background of the patient measurements to improve pathology localization, shape/size estimation and classification accuracy.

In some embodiments, the process includes detecting an antenna error or compromise from raw scattering parameters corresponding to the scattering data.

In some embodiments, the process includes detecting an antenna complete failure or partial compromise by calculating a maximum value of a logarithmic S-parameter diagonal over a frequency band of interest, and comparing individual antenna element values to a predetermined antenna error or compromise threshold value.

In some embodiments, the detected antenna(s) is(are) compromised, and the process compensates for the affected antenna by replacing its measurement results with a complex-valued average of two or more neighboring antenna measurements.

In some embodiments, the process includes generating an alert indicating which antenna(s) is(are) faulty or compromised.

In some embodiments, the process includes applying a background reference with a corresponding antenna faults(s) or compromise(s) in order to mitigate the fault/compromise.

In some embodiments, the process includes combining complex values, absolute values, real values or imaginary values of S-parameter matrices for different frequencies to generate a corresponding S-matrix for the direct mapping.

In some embodiments, the process includes determining an anatomical boundary of the object for dielectric template generation.

In accordance with some embodiments of the present invention, there is provided at least one computer-readable storage medium having stored thereon at least one of: (i) processor executable instructions and (ii) gate configuration data, which, when executed by at least one processor and/or used to configure gates of a field-programmable gate array, cause the processor and/or the configured gates to execute any one of the above processes.

In accordance with some embodiments of the present invention, there is provided an apparatus for electromagnetic imaging, including:

a memory; and at least one processor and/or logic components configured to execute any one of the above processes.

Also described herein is a computer-implemented process for electromagnetic imaging, the process including the steps of:

accessing scattering data representing at least a two-dimensional array of measurements of electromagnetic wave scattering by internal tissues of an object, wherein each said measurement represents scattering of electromagnetic waves emitted by a corresponding antenna of an array of antennas disposed about the object as measured by a corresponding antenna of the array of antennas; and processing the scattering data to generate image data representing a spatial distribution of internal features of the object, wherein the generation of the image data does not involve tomographic reconstruction but is in accordance with a weighted mapping corresponding to a spatial distribution of electromagnetic radiation emission from each said antenna to directly map the measurements of electromagnetic wave scattering to a corresponding spatial distribution of electromagnetic wave scattering by the internal features of the object that corresponds to the physical shape of the object to enable the detection, localization, size estimation and classification of one or more features of interest of the object.

BRIEF DESCRIPTION OF DRAWINGS

Some embodiments of the present invention are hereinafter described, by way of example only, with reference to the accompanying drawings, wherein:

FIG. 1 depicts various examples of suitable coordinate/grid systems in accordance with embodiments of the present invention, including: (a) a complex grid based on the antenna radiation pattern iso-contour lines, (b) a triangular finite-element like grid in elliptical form, (c) a circular grid, (d) an example of a dedicated head template/mask based spider-web grid, (e) a cylindrical grid, (f) a spherical coordinate grid, (g) an ellipsoidal grid and (h) a finite element tetrahedral grid, wherein (a-d) are examples of two-dimensional grids, and (e-h) are examples of three-dimensional grids.

FIG. 13 illustrates two examples of S-parameter data (magnitudes) of canonical samples with stroke dielectric properties near antenna 10 (left column) and antenna 4 (right column) of a fourteen channel microwave antenna array system with an elliptical container as the propagation medium: (a) raw collected S-parameter matrix, (b) S-matrix of the homogeneous background reference with average head dielectric properties, (c) result of subtracting the background reference S-matrix from the raw collected data S-matrix, and (d) results of applying eigenvalue and eigenvector decomposition to the raw collected data.

FIG. 17 illustrates the frequency domain integration of S-matrices as complex valued or absolute valued systems.

FIG. 18 includes images of dielectric tissue distributions of healthy and pathology affected anatomies such as human head generated by the processes described herein.

FIG. 19 is a set of cross-sectional plan view images of a subject's head at different offsets relative to the geometric centre of the antenna array, generated by the direct mapping process described herein and demonstrating that they can be used to detect and determine the offsets.

FIG. 20 is a screenshot of a he Graphical User Interface (GUI) of the apparatus described herein, and for displaying pathology images (such as stroke) on top of a dielectric domain (such as human head, water container or plastic head phantom). The GUI facilitates loading of patient/object/reference data and selection of desired process settings.

FIG. 23 shows: (a) a finite element grid arrangement, (b) the corresponding node/surface based complex S-parameter intensity mapping, and (c) an example of the end result of Cartesian S-matrix to finite element grid weighted mapping of S-parameters shown as a normalized magnitude plot, (d) is the elliptical finite element grid arrangement, (e) is an example of the intensity map for the grid in (d), and (f) is the electromagnetic field congruent iso-contour line finite element line structure for a single antenna.

FIG. 24 is an example of a healthy volunteer reference (HVR) database that contains 'DMM' generated images reflecting the nature of the background field, and for the purpose of finding a reference, or combination of references, that most closely match the DMM-processed field map of the patient, for use as an optimal background reference.

FIG. 25 illustrates the successful use of a healthy volunteer reference (HVR) for background field removal/mitigation and thus improved stroke detection: (a) example of a synthesis of a patient dataset and mitigation of the background field using a separate healthy volunteer reference, (b) the application of different weighted combinations of healthy volunteer references.

DETAILED DESCRIPTION

Figure 2:
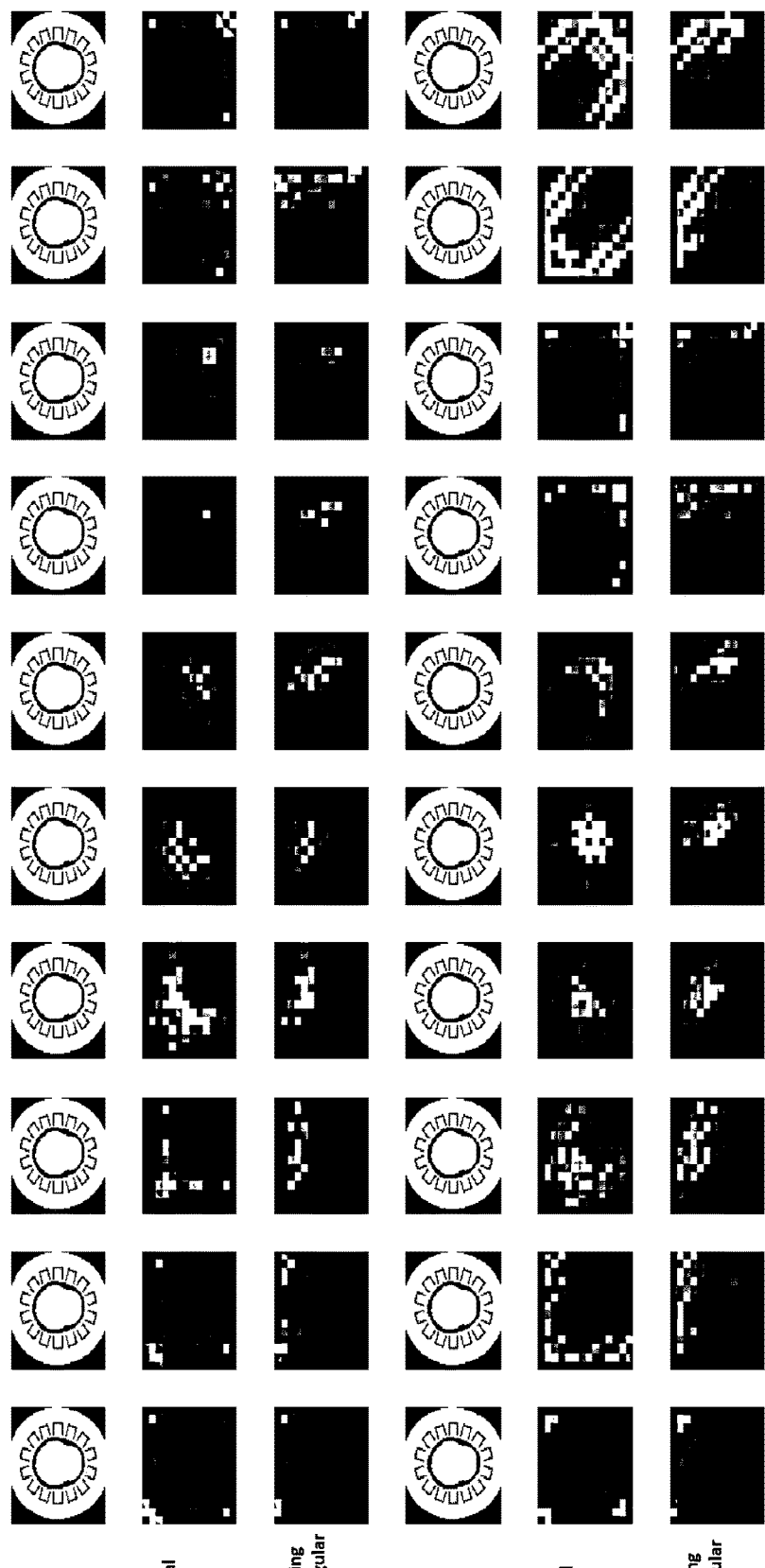
FIG. 2 is an array of images illustrating stroke imaging, wherein the first and fourth rows are cross-sectional plan views of an antenna array disposed about a patient's head, with stroke features in different locations, and the other rows are corresponding images of the full (second and fifth rows) and upper triangular (third and sixth rows) S-parameter matrices representing the stroke signal magnitude.

Surprisingly, the inventors have determined that it is possible to process electromagnetic wave scattering measurements as currently used for tomographic imaging to generate images of internal features of objects, but without requiring the application of any tomographic imaging method or electromagnetic field solver to those measurements. Instead, embodiments of the present invention process electromagnetic wave scattering measurements from an object in a relatively straightforward manner to directly map the measurements to a corresponding spatial distribution of electromagnetic wave scattering from internal features of the object. In the case of the object being a body part, the spatial distribution represents electromagnetic wave scattering by the internal tissues of the body part, and corresponds to the physical shape of the body part to enable the detection, localization, size estimation and classification of abnormal tissues within the body part. In an embodiment of the present invention, the scattering parameter data are weighted and mapped in accordance with the spatial electromagnetic radiation pattern and corresponding field interaction of the transmitting and receiving antenna pairs, as part of the multi-static Sii and Sij-parameter generation and acquisition process. In particular, the resulting spatial distributions can be viewed as images and used to detect, localize, estimate the size of, and classify strokes in human subjects.

In tomographic electromagnetic imaging, an array of antennas is disposed about an object to be imaged. Measurements of electromagnetic scattering are made by energizing each antenna of the array in turn to emit a pulse of radiation, and measuring the scattering of that pulse by the object as independently measured by each antenna of the array (including the antenna that emitted the pulse). Where the array is a two-dimensional array, the resulting measurements are stored in (or at least are equivalent to) a two-dimensional array of (complex) measurement values, also referred to in the art as 'scattering parameters'.

The direct mapping from the array of scattering measurements to a corresponding spatial distribution is performed ideally in accordance with a predetermined weighted mapping corresponding to a known (e.g., previously measured or modelled) spatial distribution of electromagnetic radiation emission from each antenna of an antenna array. However, if the spatial distribution of the electromagnetic field within the object is largely unknown or is difficult to measure/estimate, a set of weighting coefficients can be determined at the construction time of the antenna array based on a calibration of the process described herein against at least one known target ground truth as reference. During such an alternative coefficient calibration, the optimal weighting coefficients can be obtained by autonomous or manual optimization, or both.

By using direct mapping and avoiding the need for complex tomographic calculations and electromagnetic field solvers, the described process and apparatus can generate medical images from electromagnetic scattering measurements in a fraction of a second (i.e., essentially instantaneously) in comparison with prior art tomographic methods requiring from many minutes to hours to generate such images. This provides a substantial advance in electromagnetic imaging, and in emergency medical situations such as stroke detection and assessment, the resulting improvement in imaging efficiency could result in critical improvements in medical outcomes, including the difference between life and death of patients with brain injuries such as stroke or trauma. Additionally, the direct mapping circumvents any errors or inaccuracies introduced by the use of a tomographic software, and avoids the need to match the tomographic forward or inverse solvers with the experimental configuration (i.e., it also does not require tedious and long-term unreliable software calibration and/or optimization).

Some embodiments of the present invention are described herein in the context of medical imaging of body parts, in particular the human head. However, it will be apparent to those skilled in the art that the apparatus and processes described herein can alternatively be applied to generate images of internal features of other types of objects, with appropriate selection of electromagnetic radiation bandwidth.

In the described embodiments, the direct mapping of scattering measurements to a spatial distribution is a mapping to polar (or elliptical) coordinates in two dimensions, or to cylindrical, ellipsoidal or spherical coordinates in three dimensions (depending on whether the arrangement of antennas is a two-dimensional array, or a three-dimensionally array), as these coordinate systems are often more congruent with the curved geometry of the human head (or other body part that is being investigated), and thus facilitate visualization and classification of the target pathology.

It should be noted, however, that the scattering measurements (being in the form of S-parameters recorded as Sii and Sij matrix entries in the described embodiments) can also be mapped onto dedicated head-template coordinates, which can be in the form of any mesh arrangement, ranging from triangular, rectangular, hexagonal, and any higher-order polygonal shape in 2-dimensions, or alternatively tetrahedral, cubical and multi-hedral in 3-dimensions (i.e., finite element based grid arrangements), as long as the mapping approximately conforms to the head geometry.

For example, FIG. 1 illustrates various examples of suitable coordinate systems, including: (a) a complex grid based on the antenna radiation pattern iso-contour lines, (b) a triangular finite-element like grid, (c) a circular grid, (d) an example of a dedicated head template/mask based grid, (e) a cylindrical grid, (f) various spherical coordinate grids, (g) an ellipsoidal grid, and (h) a finite element tetrahedral grid. It is noted that FIGS. 1(a) to (d) (top row) and FIG. 1 (e) to (h) (bottom row) are coordinate system grids that correspond to two dimensional and three-dimensional system arrangements, respectively. For instance, a three-dimensional coordinate/grid system may be more suitable for a three-dimensional arrangement of antennas around the head or other body part, and similarly a two dimensional coordinate/grid may be more suitable for circumferential in-plane arrangements of antennas with in-plane field propagation assumptions (i.e., the fields are assumed to be invariant with respect to the z-axis orthogonal to the plane defined by the antenna array).

Another advantage of the described process and apparatus is that they can be applied without any background reference by employing the principles of raw S-parameter matrix decompositions based on eigenvalue/eigenvector linear algebra (or other forms of decomposition such as Schur or singular value decomposition (SVD)), and/or the application of a brain symmetry reference in polar (or related) coordinate systems as a direct way of subtracting one side of the brain signals from the other side (assuming sufficient brain symmetry under electromagnetic conditions wherein the working electromagnetic wavelength is larger than most of the discrepancies in tissue compartments and morphology between the two sides of the brain).

Alternatively, the described process and apparatus can be applied with any type of background reference (including homogeneous, inhomogeneous and/or virtual/digital, or any combination thereof) in order to remove or at least attenuate any signal reflections or attenuations from normal tissue, and thereby yield a stronger signal response from the abnormal tissue target. Additionally, the matrix decomposition and/or brain symmetry approach can still be performed following the use of a background reference to mitigate the (typically undesired) signals from normal tissue. In practice, the application of a suitable background reference to subtract the background electromagnetic field is applied first, followed by the brain symmetry processing applied as a second reference to yield improved results.

While the combination of background and brain symmetry reference applications is found to yield the most optimal results in practice, other references and reference combinations are also possible. For instance, some embodiments employ a reference based on a healthy volunteer (i.e., the S-parameter data of a healthy individual is used as the background field). A database of healthy volunteers can be formed by performing a large number of measurements and storing them in a lookup table. In order to select the optimal healthy reference from the database, the direct mapping process described herein can be applied to each individual raw measurement data to generate (and optionally visualize) the corresponding background field distribution/influence. The one that most closely matches that of the patient can be selected by quantifying the statistical similarity of each background field to that of the patient. To further improve the reference background, multiple healthy volunteer references can be combined as a weighted average in order to produce a virtual healthy volunteer reference (i.e., a virtual S-parameter dataset) that best matches that of the patient. This allows a matching tissue morphology to be estimated without performing actual imaging of the tissue morphology as would be the case with MRI or CT. Instead, the healthy volunteer references(s) can be compared with the measurements of the patient, qualitatively and/or quantitatively. In some embodiments, the comparison to healthy volunteer references can be accomplished directly by comparing the raw S-parameter matrices, albeit this only enables a quantitative comparison. Alternatively, the described processes can provide a qualitative assessment of the domain morphology by displaying the field map in polar space, or alternative geometrically congruent space, using the described process.

Since there are a number of frequencies at which N×N S-parameters (or other type of scattering parameters) are measured, to select the optimal frequency or frequencies for the mapping to polar coordinates (or other non-Cartesian coordinates, such as elliptical, ellipsoidal, cylindrical or spherical, for example), a maximum or minimum of the average $S_{ii}$-parameter (i.e., the S-matrix diagonal) is selected as the optimal frequency (or frequencies). Similarly, the maximum of the average $Z_{ii}$-impedance as a function of frequency can be used as an alternative optimal frequency.

In practice, the integration of the absolute-value and complex-valued S-parameters across the frequency band of interest, before the application of the S-matrix to any particular geometrically congruent space, such as for example the polar coordinate space for head imaging, has been found to yield robust results.

The classification of stroke for instance, based on the ability to differentiate an ischemic stroke from a hemorrhagic stroke, can be performed through a straightforward statistical operation utilizing the mean, standard deviation (STD) and/or variance (among others), prior to and/or after the application of the S-matrix to a body congruent geometric space of choice, from which a threshold value can be selected as a classification parameter that can differentiate one type of stroke from the other.

An embodiment of the present invention will now be described in the context of a mapping to polar coordinates, although it should be understood that other mapping/weighting techniques can be employed in other embodiments to map S-parameter matrices to other coordinate systems.

FIG. 2 is a two-dimensional array of images that includes two (the first and fourth) rows of cross-sectional plan views of a two-dimensional circular antenna array disposed about a heterogeneous head template of a human subject with stroke regions in twenty different locations of the brain, as well as respective rows of corresponding images generated by mapping the full (second and fifth rows) and upper triangular (third and sixth rows) S-parameter matrices of the scattering signal magnitude (obtained after subtraction of a background reference), illustrating the corresponding different spatial distributions of stroke signals from the S-parameter matrix as a function of the spatial location of the stroke regions within the subject's head. It is noted that this information can be suitably translated to a polar coordinate system (or similar) as it conforms to the elliptical/circular arrangement of array antennas around the subject's head in this case.

Figure 3:
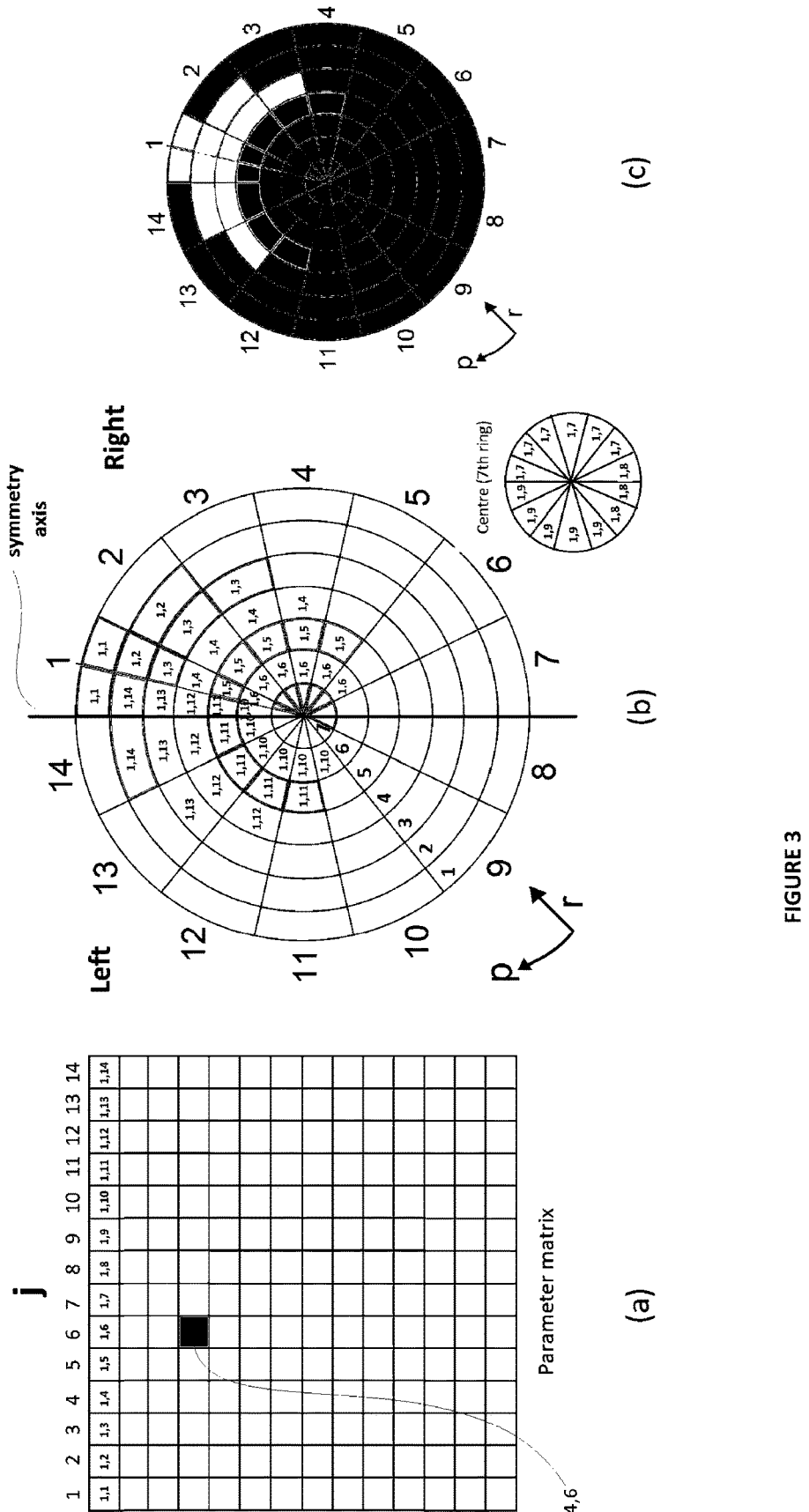
FIG. 3 illustrates an example of a Cartesian S-parameter matrix mapping or transformation to polar coordinates for an array of N=14 antennas and a corresponding 14×14 matrix of complex S-parameter data values (a), (b) illustrating an example of the Sii and Sij direct weighted mapping of S-parameters from Cartesian to polar coordinates, and (c) the corresponding spatial radiation (sensitivity) pattern of the antenna corresponding to the mapping shown in (b).

FIG. 3 illustrates an S-parameter matrix (FIG. 3 (a)) transformation to polar coordinates (FIG. 3 (b)) with N×N/2 grid points. From FIG. 3 (a) in the present example, N=14 (i.e., the number of antennas in the array), and there are 14×14 complex S-parameter data points in the S-matrix, FIG. 3(a) indicating the location of an example signal entry $S_{4,6}$. FIG. 3 (b) is an example of an S-parameter mapping (with weighting factors calculated according to the example pseudo-code given below) based on an approximate antenna (in this example, antenna number 1) spatial radiation pattern shown in FIG. 3 (c). From example FIG. 3 (b) in particular, it is noted that each polar cell is carefully assigned a scattering pair Sij (or Sii for self-reflection) that best matches the interaction of the transmitting antenna (in this example, antenna number 1) with a neighboring antenna or antennas. (For example, cell entry '1,2' refers to a parameter assignment such as $S_{1,2}$) Other suitable arrangements and methods for assigning the matrix S-parameters to a polar (or other geometric) space are possible and are not limited by the example illustrated in FIG. 3, that generically relates to the weighted direct mapping assignment of electromagnetic parameters to a body congruent grid space (various examples of which are shown in FIG. 1).

To yield a single output image, the mapping procedure according to FIG. 3 (b) is repeated for each antenna in the array, and the resulting intensities are then combined. There are different ways to accomplish this combination. In one example of the described process, for each antenna in the array, this can be accomplished by summing the values from azimuthal cells from each polar ring to yield a single intensity value that is then assigned to the polar cell with coordinates (r-index, φ-index), wherein the φ-index is equal to the antenna number. This produces integrated intensity values along a single radial cell-line (akin to a slice of a pie), and the radial cell-lines for each antenna in the array are then aggregated to generate a single output image. In another example, in order to yield a single image, the mapping procedure according to FIG. 3 (b) is first repeated for each antenna in the array, and the resulting N-maps, wherein N is the number of antennas in the array, are summed at the overlapping cell regions to generate a single output image. As described above, there are other ways for both mapping the parameter matrix entries to a geometrically congruent space and combining the resulting maps to generate a single output image.

From FIG. 3, in general, the spatial radiation (sensitivity) pattern of an antenna for weighting purposes can be determined by: (i) electromagnetic simulation of field-tissue interactions based on Maxwell's equations, (ii) sensor based measurements, (iii) analytical or analytical-numerical formulation and/or (iv) diagnostic images of antenna sensitivity maps such as those generated using any of the various sensitivity mapping methods of MRI, (such as those described in K. P. Pruessmann et al, *SENSE: Sensitivity Encoding for Fast MRI, Magnetic Resonance* in Medicine 42:952-962 (1999) and in Trakic et. al., *Image Reconstructions with the Rotating RF Coil*, Journal of Magnetic Resonance Volume 201, Issue 2, December 2009, Pages 186-198), and which can image both the magnitude and the phase of an antenna H and/or E-field in-vivo or in-vitro. These field sensitivity maps, which can have very complex spatial distributions due to field-tissue interactions at high-frequencies, can provide ideal weighting factors for the S-parameter weighted transformation from S-matrices to polar/cylindrical (or other) S-matrix indexed spaces, and thereby provide a visual depiction of the stroke location that can be suitably overlaid on top of a head/brain image or template.

In practice, if it is difficult to determine the spatial distribution of the antenna electromagnetic field, a set of (radial) weighting coefficients d can be used instead. These (radial) coefficients d need to be calibrated at the first use of the electromagnetic array. In order to do that, the process needs to be employed with at least one known ground truth (i.e., where the target location, size/shape and dielectric properties are known). The weighting coefficients can then optimized/calibrated either manually, semi-automatically or automatically.

Figure 4:
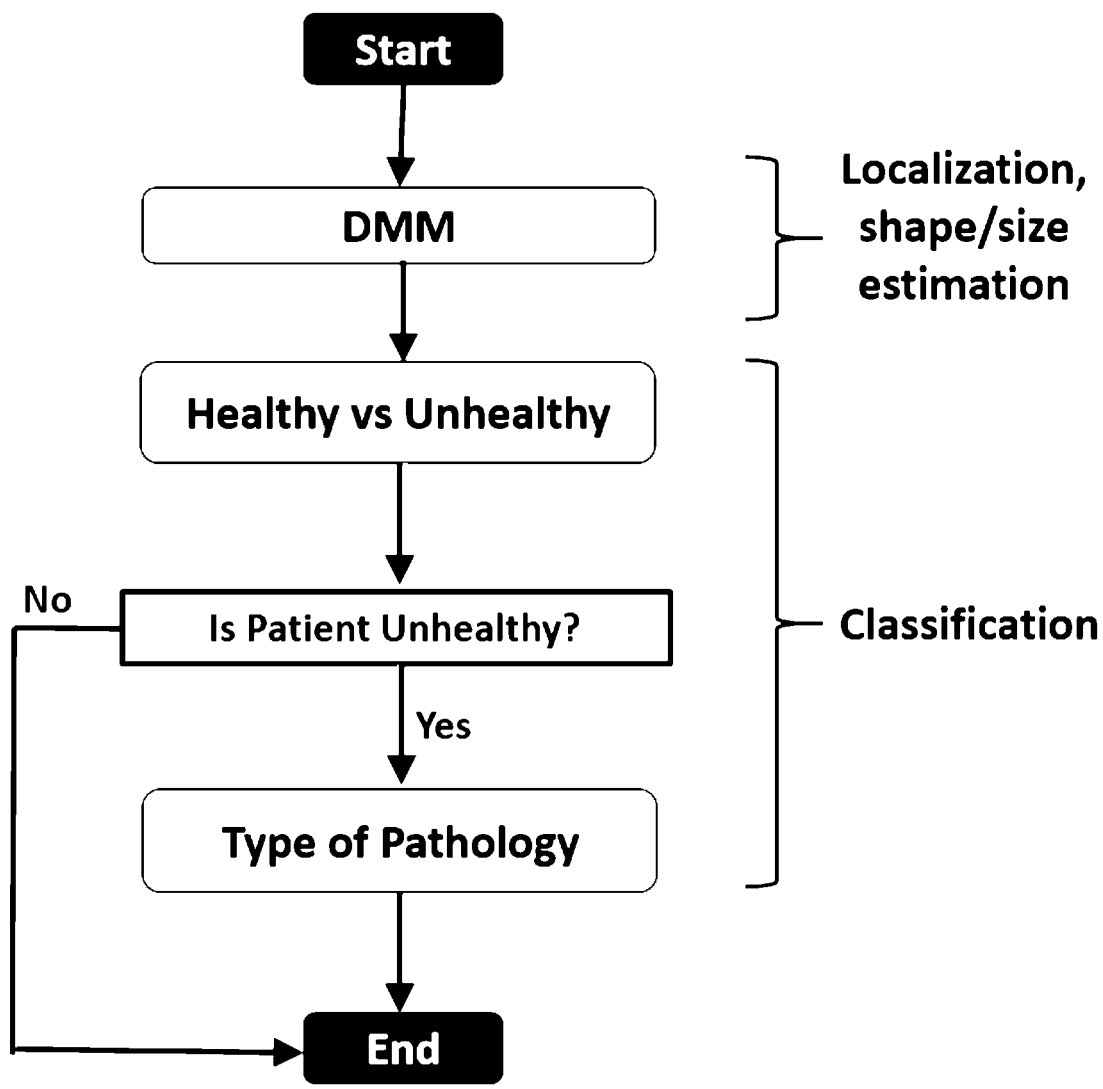
FIG. 4 is a flowchart of an S-matrix to polar space mapping or transformation process (also referred to herein for simplicity as the 'direct mapping method (DMM)') in accordance with an embodiment of the present invention, followed by a classification of the patient as either healthy or unhealthy, and a further classification of the type of pathology.
Figure 7:
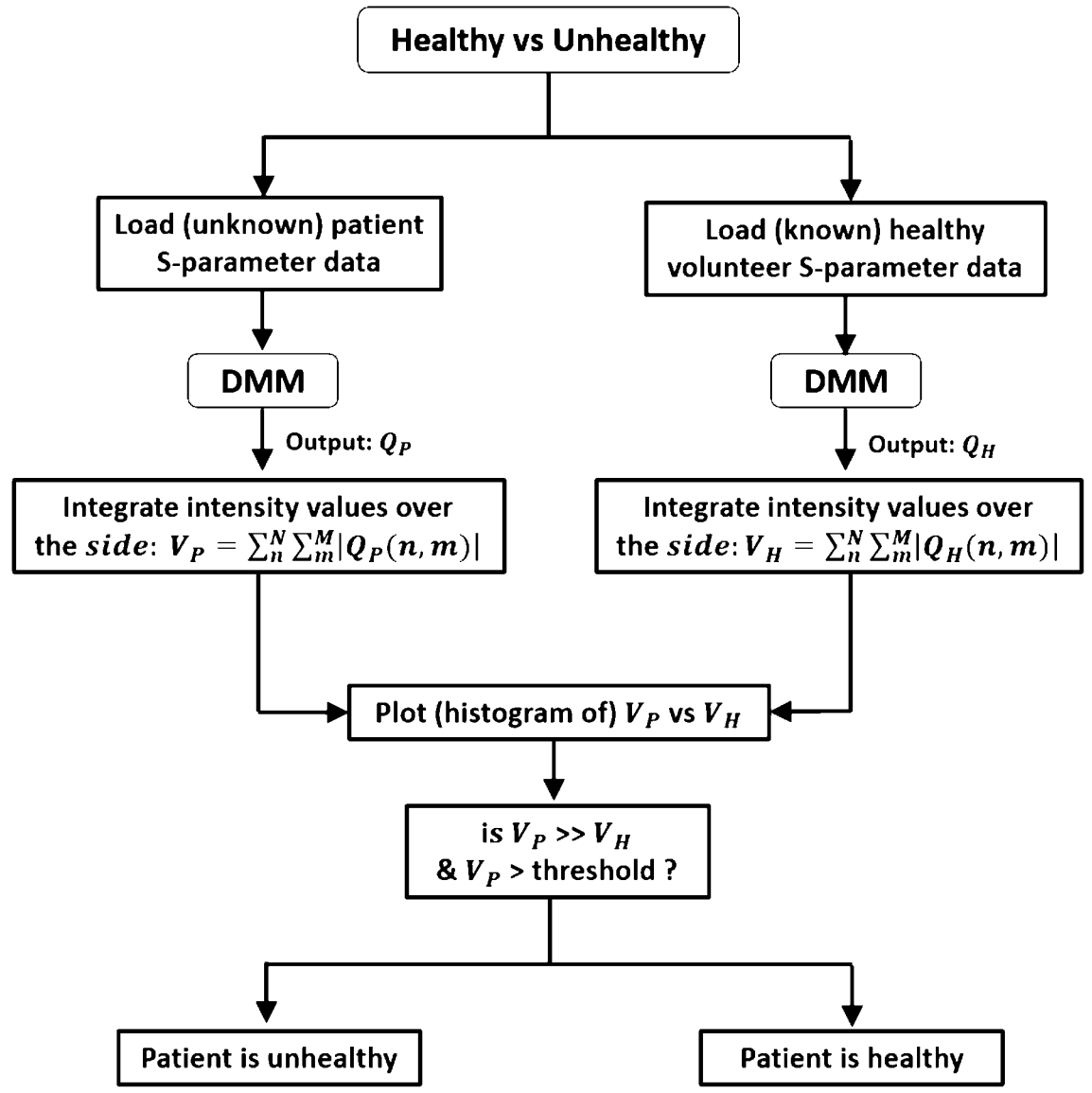
FIG. 7 is a flowchart of a 'Healthy versus Unhealthy' classification process in accordance with an embodiment of the present invention.
Figure 8:
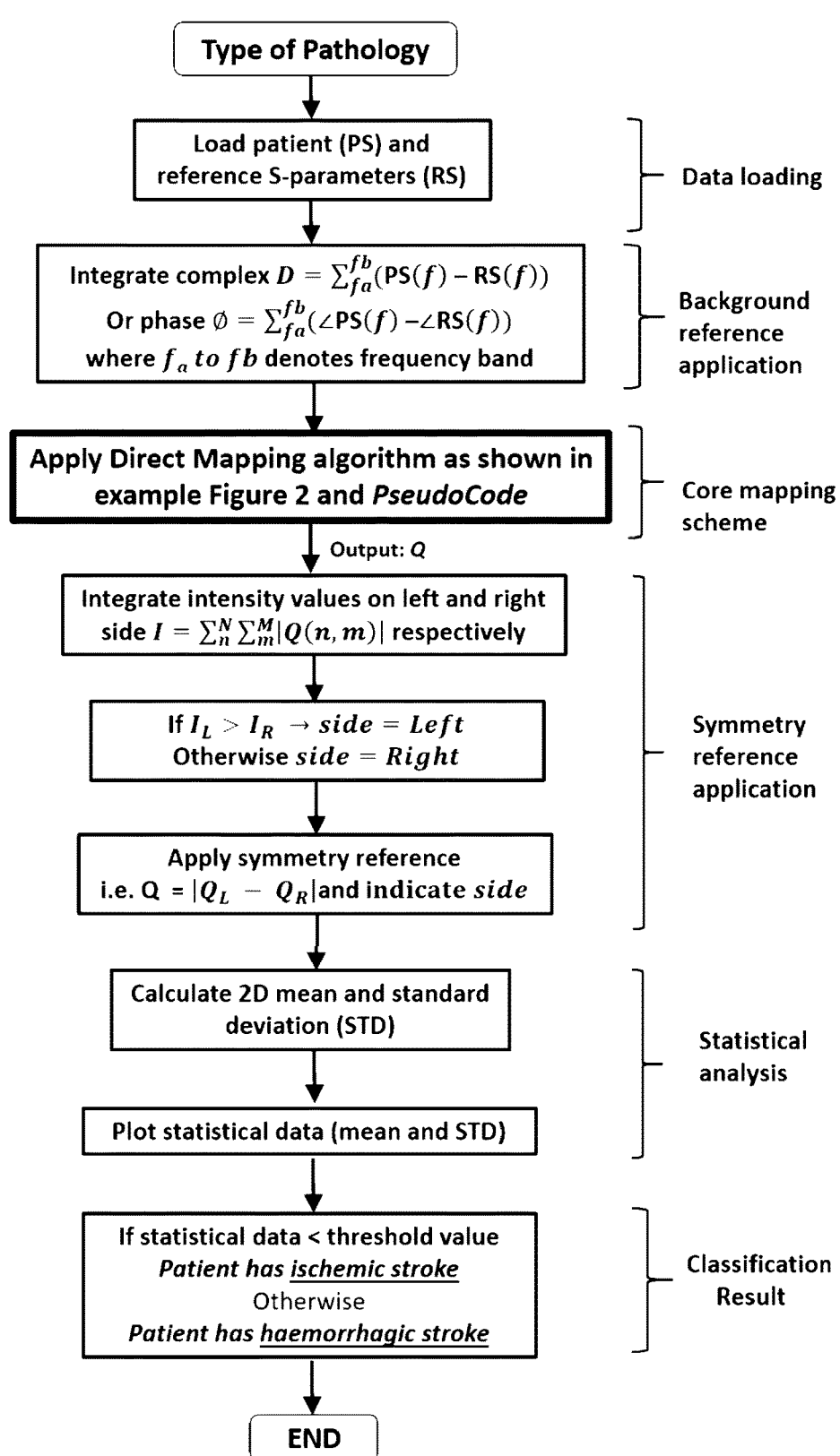
FIG. 8 is a flowchart of a 'Type of Pathology' classification process in accordance with an embodiment of the present invention, and which takes advantage of the DMM process and statistical formulations based on 2-dimensional mean and standard deviations, in order to classify the pathology in terms of pathology type. In this particular example, the classification of ischemic and haemorrhagic stroke is illustrated, although it should be understood that other types of pathologies can be classified in a similar way (e.g., tumor types).

FIG. 4 is a flowchart of a diagnostic process including the Matrix-to-polar space parameter mapping illustrated in FIG. 3 and referred to herein for simplicity as the 'direct mapping method' ("DMM")), followed by classification assessments of the patient in order to determine whether the patient is 'healthy' (i.e., has no pathology) or 'unhealthy' (i.e., has a pathology present), and if the patient has a pathology, the type of pathology is determined. Each of the curved boxes in the flowchart represents procedure sub-process; for instance the 'DMM' sub-process is represented by the flowchart of FIG. 6, the 'Healthy vs Unhealthy' assessment sub-process is represented by the flowchart of FIG. 7 and the 'Type of Pathology' assessment sub-process is represented by the flowchart of FIG. 8.

Figure 5:
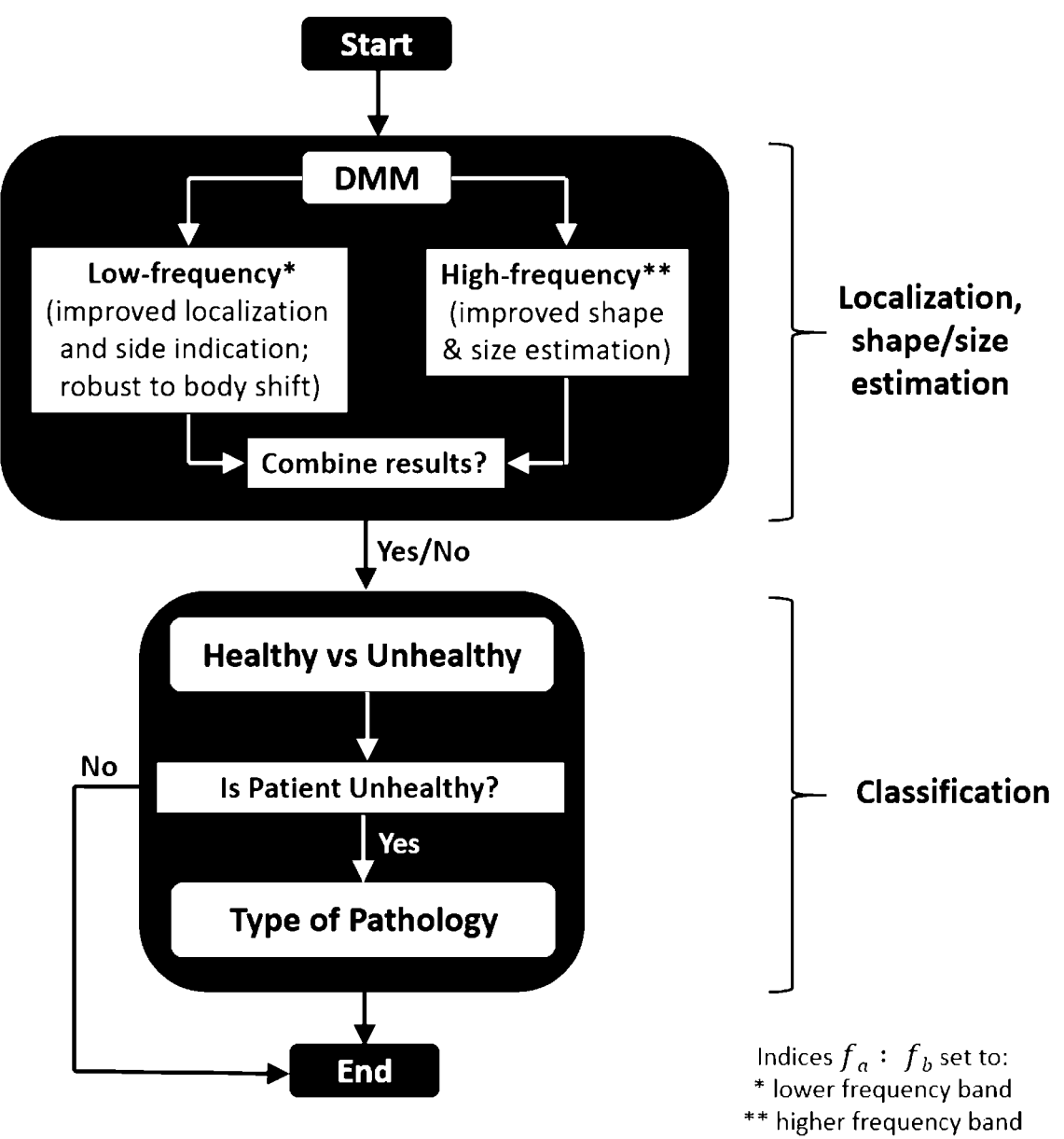
FIG. 5 is a flowchart similar to that of FIG. 4, but including two separate applications of the DMM method respectively utilizing lower and higher frequency parameters (for improved and more robust stroke side indication, localization and shape/size estimation), again followed by classification of the patient as healthy or unhealthy, and classification of the pathology.
Figure 6:
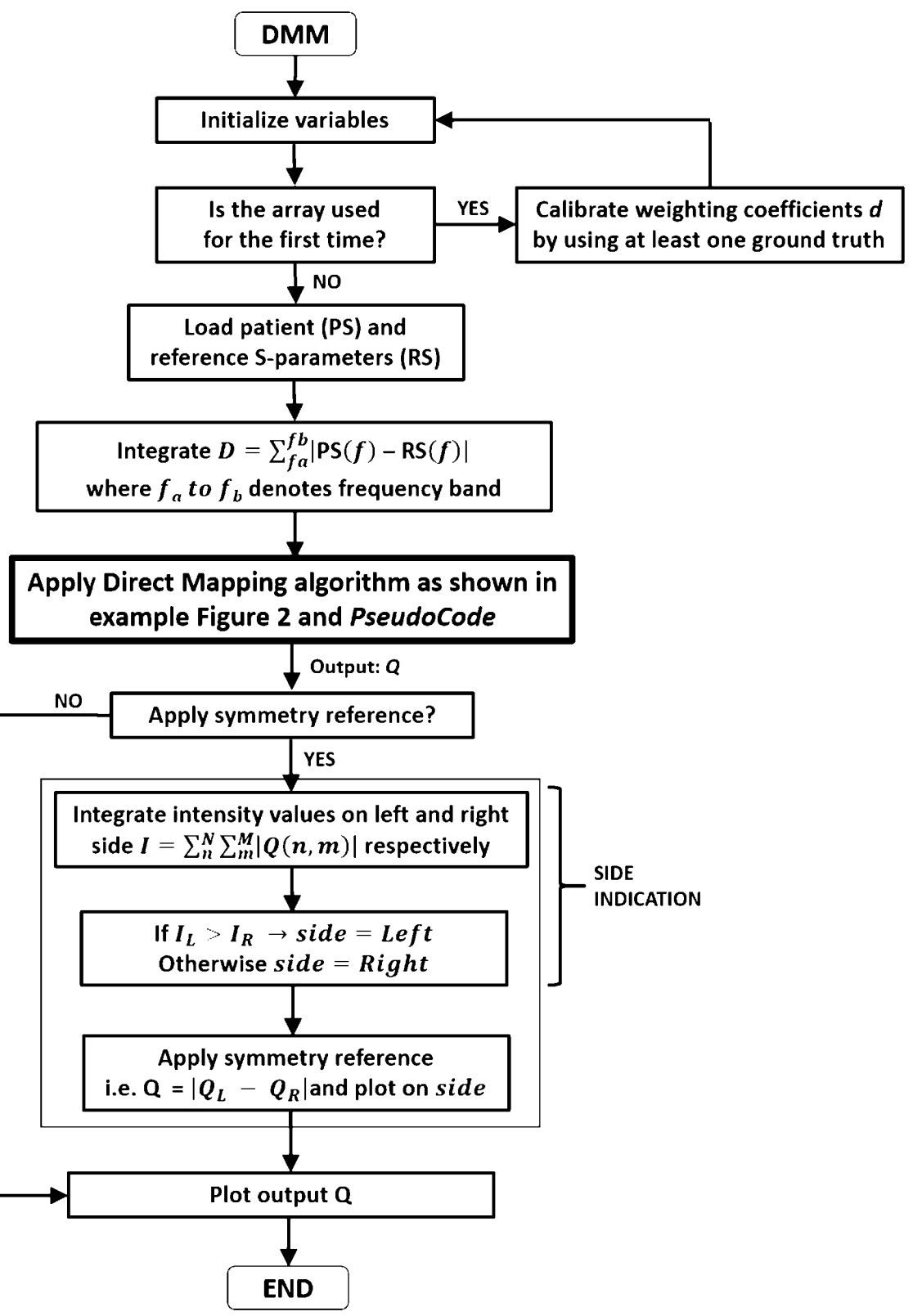
FIG. 6 is a flowchart of a DMM process in accordance with an embodiment of the present invention, and which takes advantage of a background reference and optionally also a symmetry reference. The corresponding Cartesian-to-polar space mapping process is illustrated in FIG. 3.

For the purpose of optimal localization and shape/size estimation of the target pathology, it is often useful for the DMM process to perform mathematical integration of selected frequency samples at low-frequencies (i.e., set the start (fa) and end (fb) frequencies in FIG. 6 to define a suitable low frequency range/band), because the lower frequencies are much less susceptible to body offsets or movement within the electromagnetic array and are thereby much more robust to the corresponding signal and image artefacts that result from such body offsets (especially if the body offset is along the Left-Right direction of a head, such that the head symmetry assumption may be invalidated from an electromagnetic perspective). This is illustrated in the embodiment shown in the flowchart of FIG. 5, which is a modified version of the flowchart of FIG. 4. Since the signal and image artefacts resulting from body offsets can dominate the application of the symmetry reference (including side indication), the application of low-frequencies (i.e. around 100-700 MHz) can significantly mitigate these artefacts and yield a more robust application of symmetry reference, especially where the correct side indication of the pathology is of concern. This is due to the fact that at low frequencies the electromagnetic waves do not reflect of the surface of the body as much as they do at high frequencies. The low frequency waves can more easily penetrate into the body and readily interact with the target pathology to produce target-reflected signals for image generation. While low frequency electromagnetic waves are great for initial localization and symmetry-reference-based side indication of the pathology, they are limited in producing higher resolution images of the target. The higher resolution images can be readily obtained with the use of higher frequency electromagnetic waves (i.e. around 700 MHz-2.5 GHz). Therefore, following the application of the DMM process at low-frequencies for initial target pathology localization and correct side indication estimation, the DMM process is applied independently a second time whilst employing higher frequency S-parameters, in order to provide higher spatial resolution and a more refined target shape/size.

It is important to note that the separate processing of the lower and higher frequency bands as described above is only used in some embodiments, as in general embodiments of the present invention can be applied with virtually any frequency band (i.e., low-to-high, low, mid-to-high, high, mid, etc.) in respect to the particulars of the imaging system and environment. Therefore in general the 'DMM' process can be applied only once or multiple times (with different settings), and in the latter case the results are weighted or averaged to yield an optimal imaging result.

FIG. 6 is a flowchart of the 'DMM' process of FIGS. 4 and 5 in accordance with an embodiment of the present invention. If spatial maps of the antenna are not available, and the electromagnetic system is being used for the first time (or needs re-calibration due to system/hardware change or other reason), then the (radial) weighting coefficients d are calibrated/optimized against at least one known ground truth before the imaging process begins. Thereafter, the patient and (background) reference S-parameter measurement data are loaded. The complex valued S-parameters of the (background) reference are subtracted from those of the patient at every frequency point, and the resulting difference is integrated over a selected frequency band of interest. This is then followed by the direct mapping process as illustrated in example FIG. 3 (and provided pseudocode), the output of which can be directly plotted. Optionally, at this point, the symmetry reference can be also applied to yield a further improvement in the results and a reduction in background-field related artefacts and noise. To do so, first the intensity values on each side of the symmetry are integrated and the resulting sums are compared. If the intensity on one side is larger than the other, then it is very likely that the target pathology will be located on the side with the greatest intensity. This then indicates the side of the symmetric body part (e.g., such as a human head) which is to be plotted. In order to apply the symmetry reference, the intensity distribution on one side of the symmetry axis is subtracted (e.g., polar cell-by-cell) from the corresponding distribution on the other symmetric side of the body, and the result is then plotted.

FIG. 7 is a flowchart of the 'Healthy versus Unhealthy' classification process in accordance with an embodiment of the present invention, and which takes advantage of the DMM process of FIG. 6. The S-parameter data from both a healthy individual (where it is known that the individual/volunteer has no pathologies) and that of the patient (where it is not known whether the individual has a pathology or not) are processed by the 'DMM' process in accordance with FIG. 6 (and example mapping process of FIG. 3). The individual resulting intensity distributions Q (in polar space), i.e. $Q_P$ (P=patient) and $Q_H$ (where H=healthy) are integrated over the entire imaging domain, and the final results are compared to a corresponding predetermined threshold value. If the integrated intensity value from the patient's dataset is noticeably greater than the predetermined classification threshold value, then the patient is likely to have a pathology. Otherwise, the patient is classified as being (i.e., deemed to be) healthy. The findings can be further corroborated by a physician's diagnosis and assessment of symptoms, and assessed against any spatially localized phenomena in the 'DMM' process output image generated following the example procedure in FIG. 6.

FIG. 8 is a flowchart of the 'Type of Pathology' classification process in accordance with an embodiment of the present invention, and which also takes advantage of many of the 'DMM' processes, albeit with some unique adaptations. First, the patient and reference S-parameter data is loaded (assuming that the weighting coefficients, including d coefficients if used, are already calibrated and set). The reference S-parameters are subtracted from the patient S-parameters as complex values at each frequency point within a band of chosen frequencies, and the result is integrated for each S-parameter entry. The direct mapping process described above is then applied using a mapping assignment such as the one shown in FIG. 3. A symmetry reference is then applied as shown in FIG. 6. Then, 2-dimensional mean and standard deviation (and potentially variance/covariance) values are calculated and plotted against other similarly processed patient results (some of which may or may not have ground truth information). If the calculated statistical values are less than the corresponding predetermined classification threshold values, then in this particular flowchart example of stroke classification, the patient is classified to have an ischemic stroke, otherwise the patient is classified to have a haemorrhagic stroke. This is merely an example of classification, and it will be apparent to those skilled in the art that the processes described herein are not limited to the classification of stroke type, but are also able to classify other types of pathologies, such as for example types of tumor, or other tissue diseases. The processes described herein are also not limited to the specific statistical formulations described above. Similarly, with the use of direct mapping method at the core, other suitable classification processes can be performed in other embodiments.

Figure 9:
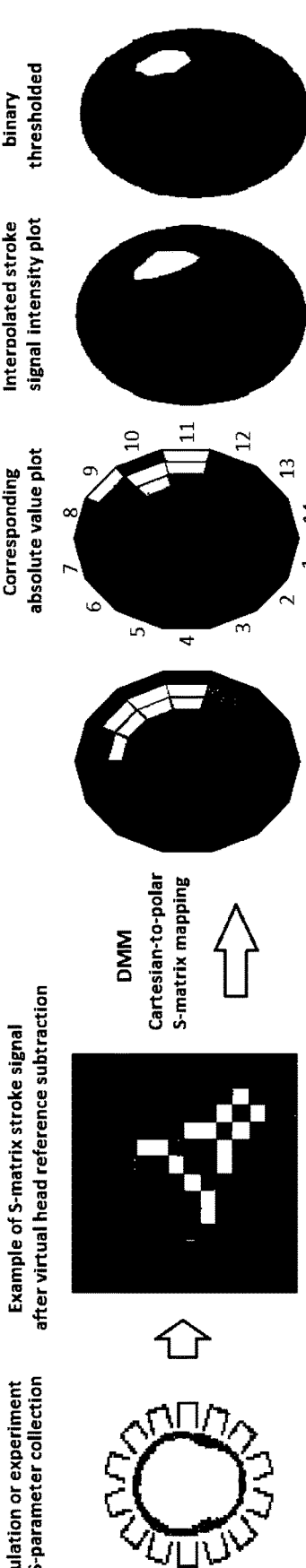
FIG. 9 illustrates the collection of complex S-parameters in Cartesian coordinates with Sii and Sij entries and the result of weighted remapping of the S-parameter data to polar coordinates in order to visualize a stroke.

FIG. 9 illustrates an example workflow wherein S-parameter data are obtained from simulation and/or experiment, and a stroke signal S-parameter matrix is derived following the subtraction of background signals from a virtual head reference (i.e., without stroke). The example transformation to polar coordinates is applied with weighting factors based on an antenna radiation pattern spatial intensity used for each antenna. The resulting polar coordinate plots are direct visual representations of the target stroke location, size, intensity, and (as described below) also the type of stroke (i.e., classification). Also shown are interpolated and binary thresholded and segmented target stroke images.

In contrast to tomographic imaging methods, which take at least many minutes to calculate a final result/solution using a high speed computer, the processes and apparatus described herein take only a fraction of a second (typically 100-300 milliseconds on a standard personal computer) to generate such images for stroke detection and assessment.

Figure 10:
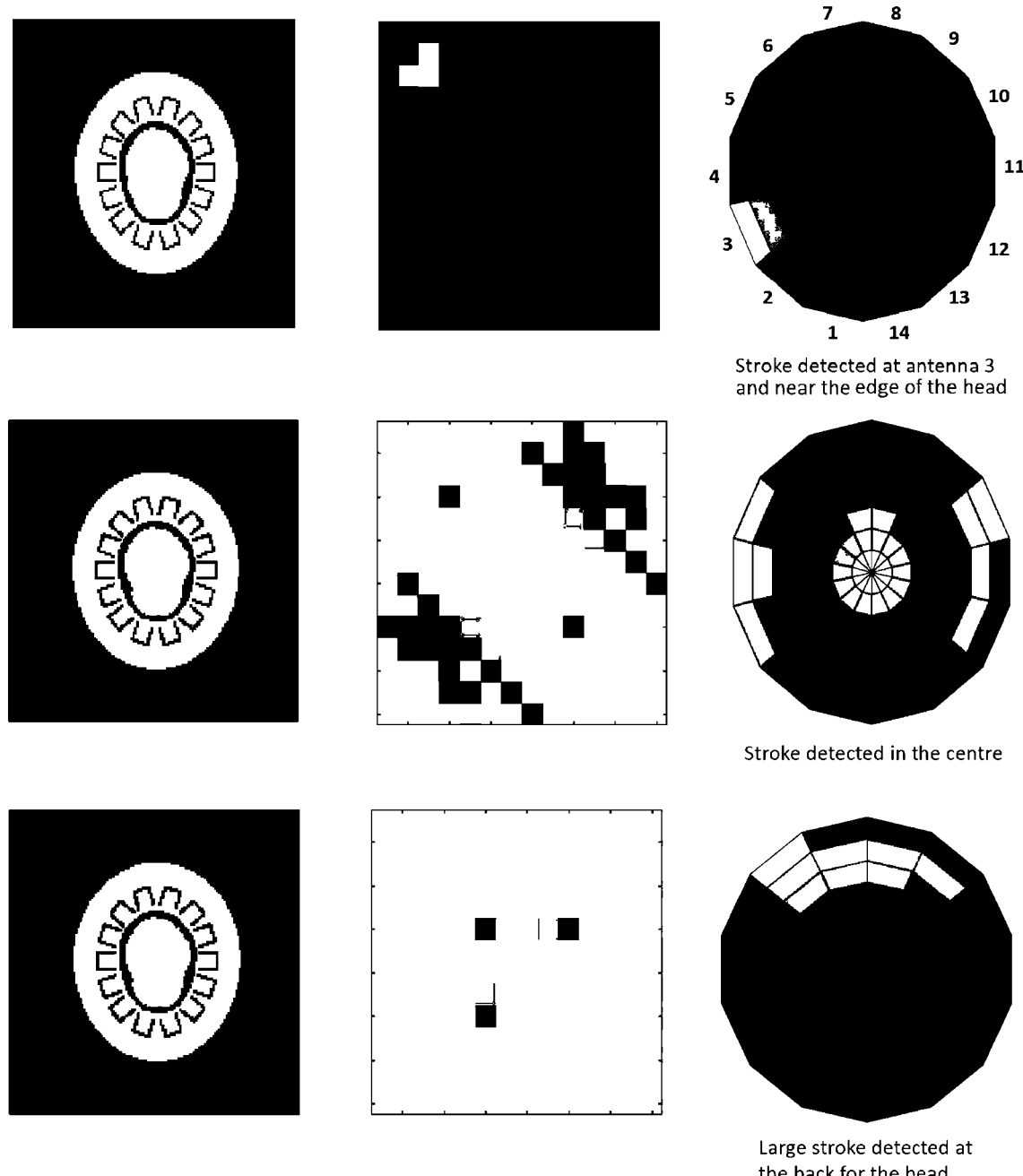
FIG. 10 shows the results (right column) of remapping S-parameter data in Cartesian coordinates (middle column) to polar coordinates based on models with different hemorrhagic stroke sizes and locations (left column).

FIG. 10 illustrates three additional examples of mapping S-parameters to spatial distributions in polar coordinates, showing (in the left column) two medium sized strokes and one larger stroke at different locations inside a head model, as well as (in the middle column) a colour map of the corresponding S-parameter matrices (using the matrix indices as Cartesian coordinates), and (in the right column) the resulting (weighted) polar plots of same. It is apparent that the polar plots generated by the process described herein correctly represent both the location and the size of the stroke in each case.

Figure 11:
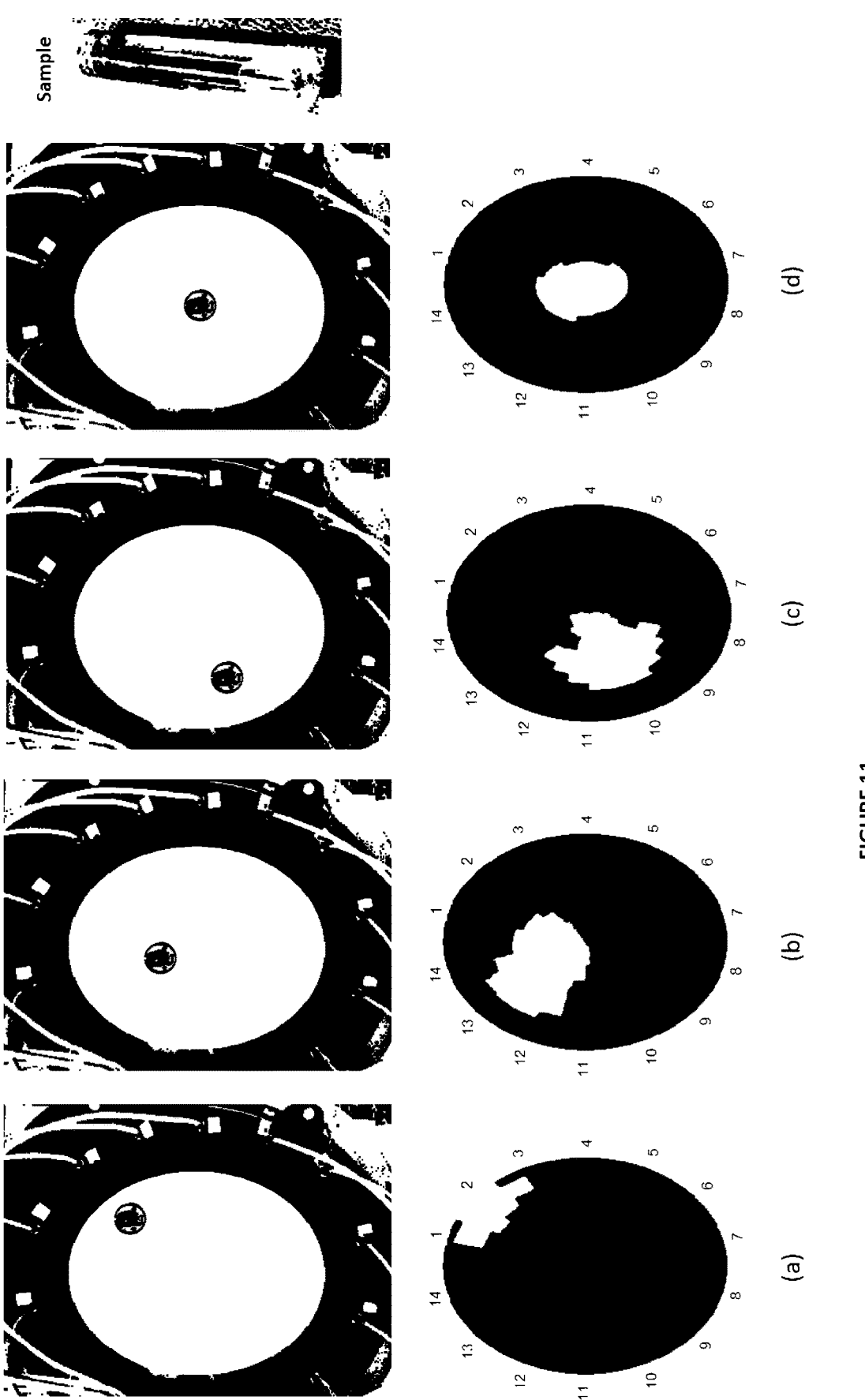
FIG. 11 compares the results of direct mapping (lower row) with corresponding images (upper row) of a dielectric target inside a water bath, surrounded by an electromagnetic antenna array, for different offsets of the target relative to the geometric of the antenna array, wherein the target is: (a) near antenna no. 2, (b) near the center and towards antenna no. 13, some distance from antenna no. 11, and (d) within the center of the imaging domain.

FIG. 11 includes images of various laboratory experiments (top row), wherein a dielectric sample was placed at different locations within an elliptical water-filled container, surrounded by a 14-channel electromagnetic array (operating between 0.5-2.0 GHz). FIG. 11 also shows the corresponding reconstructed images generated by the processes described herein, wherein the dielectric target was correctly localized within the imaging domain, including its size/shape.

Figure 12:
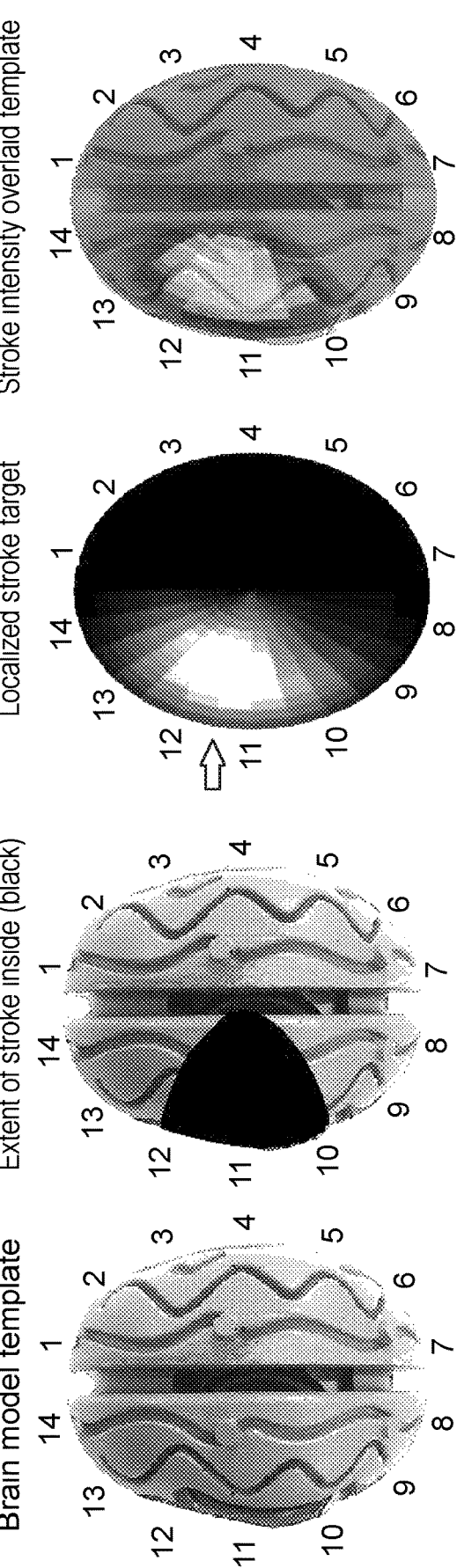
FIG. 12 shows the successful result of remapping the S-parameter data obtained in an experiment with a (3D printed) realistic heterogeneous head phantom (with several tissue types and corresponding dielectric properties), and with a large stroke spanning the right side of the brain roughly from antenna 10 to antenna 12 (indicated as a black/dark area). Also shown is the resulting stroke target intensity (generated by the process of FIG. 4-6), and the same stroke intensity overlaid on top of the image of the constructed head phantom.

FIG. 12 illustrates an example wherein a 3D-printed heterogeneous head phantom with a large stroke target spanning the right side of brain (from antenna 10 to antenna 12) was measured with a 14-channel microwave antenna array system, and the resulting S-parameter matrix was mapped to polar coordinates using weighting factors as described above. The dark area (colored in black) represents the size and shape of the target stroke within the constructed brain phantom. FIG. 12 also shows the correctly localized and sized stroke target overlaid on the anatomical image of the brain phantom.

Example pseudo-code implementing the weighted mapping of an S-parameter matrix to polar coordinates using weighting factors based on approximate antenna spatial radiation profiles is shown below:

```
N = 14; example number of antennas
A = 2 × i − 1; where i is an index into N
```

$$\text{indx}\left[\text{round}\left(\frac{N}{2}\right)\right] = [7, 6, 5, 4, 3, 2, 1];$$

```
cnt[N + A(N)] = [ . . . 9; 10; 11; 12; 13; 14; 1; 2; 3; 4 . . . ];
for i = 1:N
```

-continued $$R_1: Q(\text{indx}_1, i) = \sum_{i=1}^{N=14} \frac{w_{i,i} S_{i,i}}{d_p}$$

for a = 0:A $$R_p\{p = 2 \dots 7\}: Q(\text{indx}_p, \text{cnt}(i + a)) = \frac{1}{A} \sum_{i=1}^{N=14} \frac{w_{i,cnt(i+a)} S_{i,cnt(i+a)}}{d_p}$$

```
    end
end
```

Then, for each subcase of a:

$$\text{if } a == \text{round}\left(\frac{A}{2}\right)$$

$$RP: Q\left(\text{indx}_p, \text{cnt}(i+a)\right) = \frac{1}{A} \sum_{i=1}^{N=14} \left(\frac{W_{i,cnt(i+A)} S_{i,cnt(i+A)} + W_{i,cnt(i+0)} S_{i,cnt(i+0)}}{d_p}\right)$$

where N is the number of antennas, $R_1 \dots R_7$ are the radial sectors with $R_1$ being the outmost ring, a is an index into A, and Q is the resulting stroke intensity based on the weighted summation of complex or absolute-value S-parameter entries $S_{i,j}$ (in accordance with the antenna spatial radiation pattern coefficients w, as depicted in FIG. 3 (*c*)), and d is the alternative radial weighting coefficient vector of length N, which when used in practical application, then w=1. Otherwise, if w-coefficients are employed, then d is set to one (i.e., d=1). In some practical applications, when the weighting parameter w (size N×N/2; where N is the number of antennas) cannot be readily determined, the alternative artificially-introduced weighting parameter d, which has a much shorter length of N/2, can be used instead. The two weighting parameters sets are generally intended to be mutually exclusive, with one of the two sets selected depending on the practical case scenario (i.e. they are not meant to be used together, although they could be). The weighting parameter d however, needs to be manually, semi-automatically or automatically optimized/calibrated by using the described process on at least one known ground truth.

Also it is noted that within the pseudocode, the $S_{i,j}$ values can be replaced with corresponding $\Delta S_{i,j}$ values, which denote the S-matrix values where the signal data from a reference has been subtracted from the measured S-matrix with the stroke.

The stroke S-parameter signal (i.e., related to fields that are reflected and/or attenuated by the stroke) is very small in magnitude when compared to the raw collected S-parameter signals (i.e., related to fields that are reflected and/or attenuated by normal head tissue, which comprises the bulk of the field-propagation medium). The stroke signal is typically 30 dB to 80 dB lower in magnitude than the raw signal (i.e., typically much less than 0.5% in relative percentage signal contribution). Consequently, the stroke signal peak is not visible or obvious when directly observing the S-parameter matrix, as shown in FIG. 13 (*a*). It is often only after the subtraction of a background reference (FIG. 13 (*b*)) that the stroke target can be visibly differentiated (FIG. 13 (*c*)). As described below, eigenvector and eigenvalue decomposition of the raw S-matrix (i.e., without background reference) can be performed to accurately ascertain the location and extent of a weak stroke target signal that is dominated by signals from normal tissue (FIG. 13 (*d*)).

In various embodiments of the present invention, there are several approaches that can be used independently or in combination with each other in order to enhance the stroke signal (and that might or might not utilize a background reference), including:

(1) Subtraction of a virtual head reference S-matrix from the patient S-matrix.

(2) Subtraction of a healthy volunteer reference (HVR) S-matrix from the patient S-matrix; or instead of using a single HVR, multiple HVRs can be combined and a synthetic weighted average HVR that best approximates the patient background field (the influence of which can be plotted, visualized and assessed using the 'DMM' process), is employed.

(3) Subtraction of a dielectrically homogeneous (or polynomial varying) background reference S-matrix from the patient S-matrix.

(4) eigenvalue and eigenvector decomposition of the patient S-matrix (without any background reference) to extract information on the weak stroke signal (abnormal tissue) that is at least three orders of magnitude smaller compared to S-parameters due to normal tissue of the head.

(5) Use of brain symmetry in polar coordinates to obtain well-conditioned stroke signals without a background reference.

(6) S-matrix mapping to polar coordinates should be applied at a frequency that corresponds to the minimum and/or maximum of the average Sii-parameter frequency response.

(7) mapping to polar coordinates can be applied to both the magnitude and the phase of the S-matrix in question, whereas the phase information should be ideally defined as the absolute value of phase during the weighted mapping.

(8) Integration of S-parameter values (i.e., complex, absolute value, real or imaginary) can be performed over a frequency band of interest.

(9) Application/administration of an intravenous contrast agent that noticeably changes the dielectric properties of the target stroke and thereby leads to a better stroke-to-normal tissue contrast for the purpose of improved electromagnetic imaging. MRI and CT techniques employ analogous principles of contrast agent administration in order to improve the measured signal, signal-to-noise ratio (SNR), and/or image contrast.

(10) A combination of any or more of the above.

In some embodiments, the S-matrix of a virtual head reference (derived from segmented MRI images of the patient and simulated by an electromagnetic solver that has been validated and properly calibrated with respect to the actual system used to perform the measurements in order to obtain the S-parameters) is subtracted from the S-matrix of a patient with stroke (as shown in the example of FIG. 9). If there are no significant variations in patient head position relative to the virtual reference (post-position-optimization), then this approach provides a viable stroke S-matrix that can be mapped to polar/cylindrical coordinates. The same procedure can be also performed with a homogeneous background reference with head-averaged dielectric properties (via experiment/simulation pathways).

Figure 14:
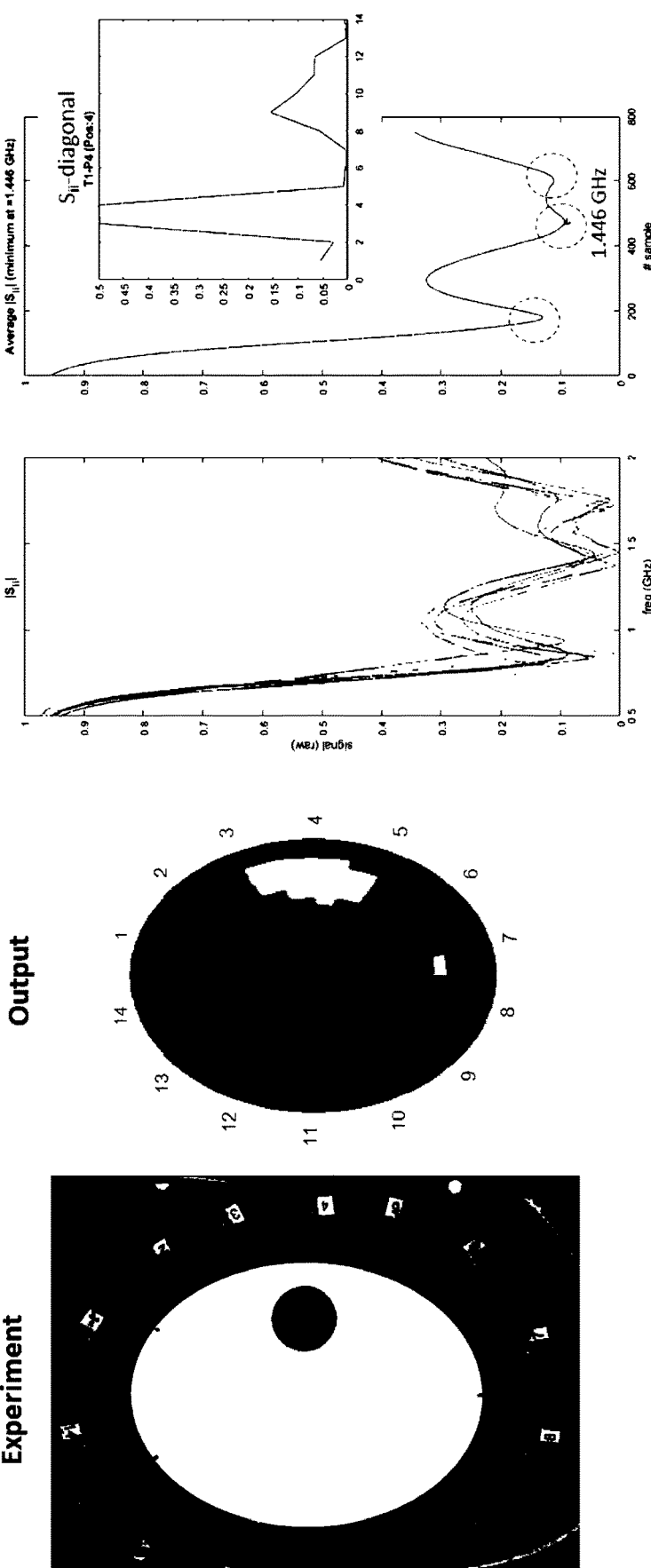
FIG. 14 illustrates the selection of an optimal frequency point for S-matrix Cartesian-to-polar mapping based on a minimum value of the average Sii frequency response.

In some embodiments, eigenvalue and eigenvector decomposition of the raw S-matrix without the need of any background reference is employed to effectively extract useful information about the signals from abnormal tissue (such as that of a stroke) which are dominated by the signals from normal tissue, and are therefore hidden in the raw S-matrix (see FIG. 13 (d) and FIG. 14). This process can be applied to extract useful information about abnormal tissues from the raw S-matrix, despite the fact that the abnormal tissue signal is about three or more orders of magnitude smaller than the signals due to surrounding normal tissues of the head, as follows:

$$Sv=\lambda v$$

where S is the complex raw S-parameter matrix (without application of background reference in this case), v is the eigenvector matrix, and $\lambda$ are the eigenvalues. The eigenvector v can be mapped to polar coordinates as described herein in order to reveal the location(s) of abnormal tissue. An alternative and equally useful process is to map the following matrix result to polar coordinates:

$$S=|v^T\lambda+\lambda^T v|$$

where T denotes transposition. It is noted that, based on the theory of eigenvector/eigenvalue decomposition, $|v^T\lambda-\lambda^T v|$ (i.e., the difference, not the sum) should equal zero. Similarly, other types of matrix decompositions and analyses, such as for example singular value decomposition (SVD) and Schur decomposition, can be performed to extract useful information about abnormal tissue. For example, given the complex S-parameter matrix S, such that:

$$S=QUQ^{-1}$$

where Q is the unitary matrix such that its inverse $Q^{-1}$ is also the conjugate transpose Q* of Q, and U is an upper triangular matrix, which is called the Schur form of S. The eigenvalues are the diagonal entries of U. Similarly, the Schur decomposed matrices can be conveniently mapped onto a polar/cylindrical grid for ease of stroke visualization/detection. It will be apparent to those skilled in the art that other linear algebra operations are also possible to achieve the same outcome.

For example, since the brain is symmetric relative to the left-right brain hemisphere axis, this can be effectively used instead of a dedicated background reference. Once the S-matrices are transformed to polar coordinates, it becomes very straightforward to subtract the left side from the right side (and vice versa) in polar coordinates, as follows:

$$\text{for } i\,|\,j=1: \left(\text{floor}\left(\frac{N}{2}\right)-1\right)\xrightarrow[end;]{do} S_{sym}(i,j)=S(i,j)-S(i,N-j)$$

where $S_{sym}$ is the resulting polar S-parameter plot following subtraction of the symmetric brain reference, and i and j refer to the indices in the radial and azimuthal dimensions, respectively. Alternatively, S can be exchanged with $\Delta S$, which denotes the S-matrix where the signal data from the reference has been subtracted from the S-matrix with the stroke.

It is noteworthy that the S-matrices also have a third dimension representing electromagnetic radiation frequency, and there are typically hundreds of frequency samples spanning a frequency band of interest. The optimal frequency (or frequencies) for the selection of the N×N 2D S-matrix for mapping to polar coordinates is (or are) determined based on the frequency (or frequencies) that correspond(s) to a minimum/maximum of the average S-parameter frequency response (in this case taken as the average of the Sii-parameter matrix diagonal data), as shown in FIG. 14:

$$f_n \triangleq \left| \frac{1}{N} \sum_{i=1}^{N} (\Delta S_{i,i}(f)) \right|_n$$

where $$f_{min} \triangleq \min(f_n) \| f_{max} \triangleq \max(f_n)$$

Equivalently, the peaks of the Z-impedance (average) frequency response line can be also considered as frequency points at which to perform the mapping to polar coordinates and thereby yield an improved polar-plot localization of the stroke target, according to:

$$f \triangleq \max \left| \frac{1}{N} \sum_{i=1}^{N} Z_0 \left( \frac{1 + \Delta S_{i,i}(f)}{1 - \Delta S_{i,i}(f)} \right) \right|$$

Figure 15:
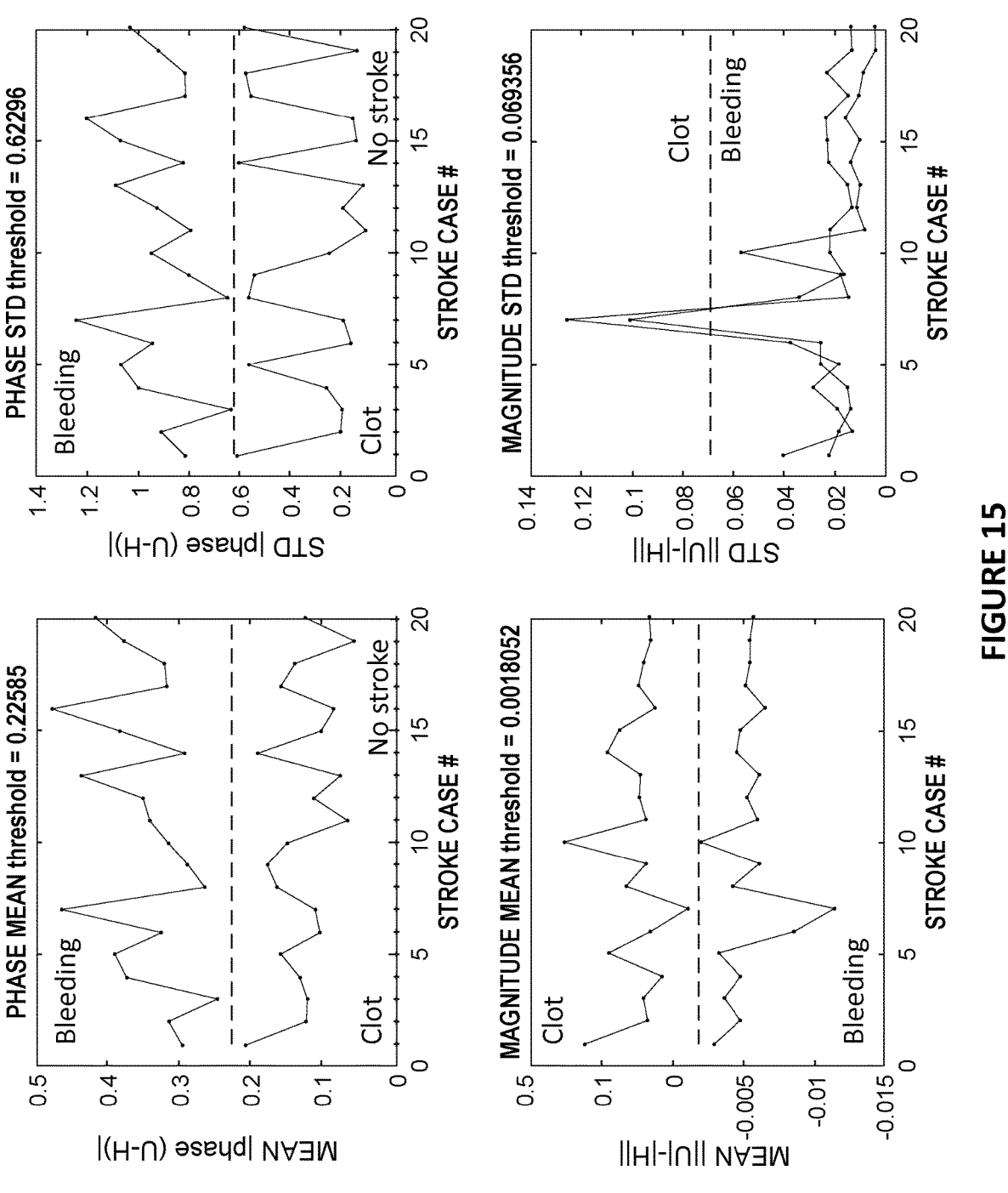
FIG. 15 are graphs of the outputs of stroke classifiers (plotted here as thresholds) based on mean and standard deviation parameters of magnitude and phase S-parameter data for a total of twenty (20) (hemorrhagic or clot) stroke cases.
Figure 16:
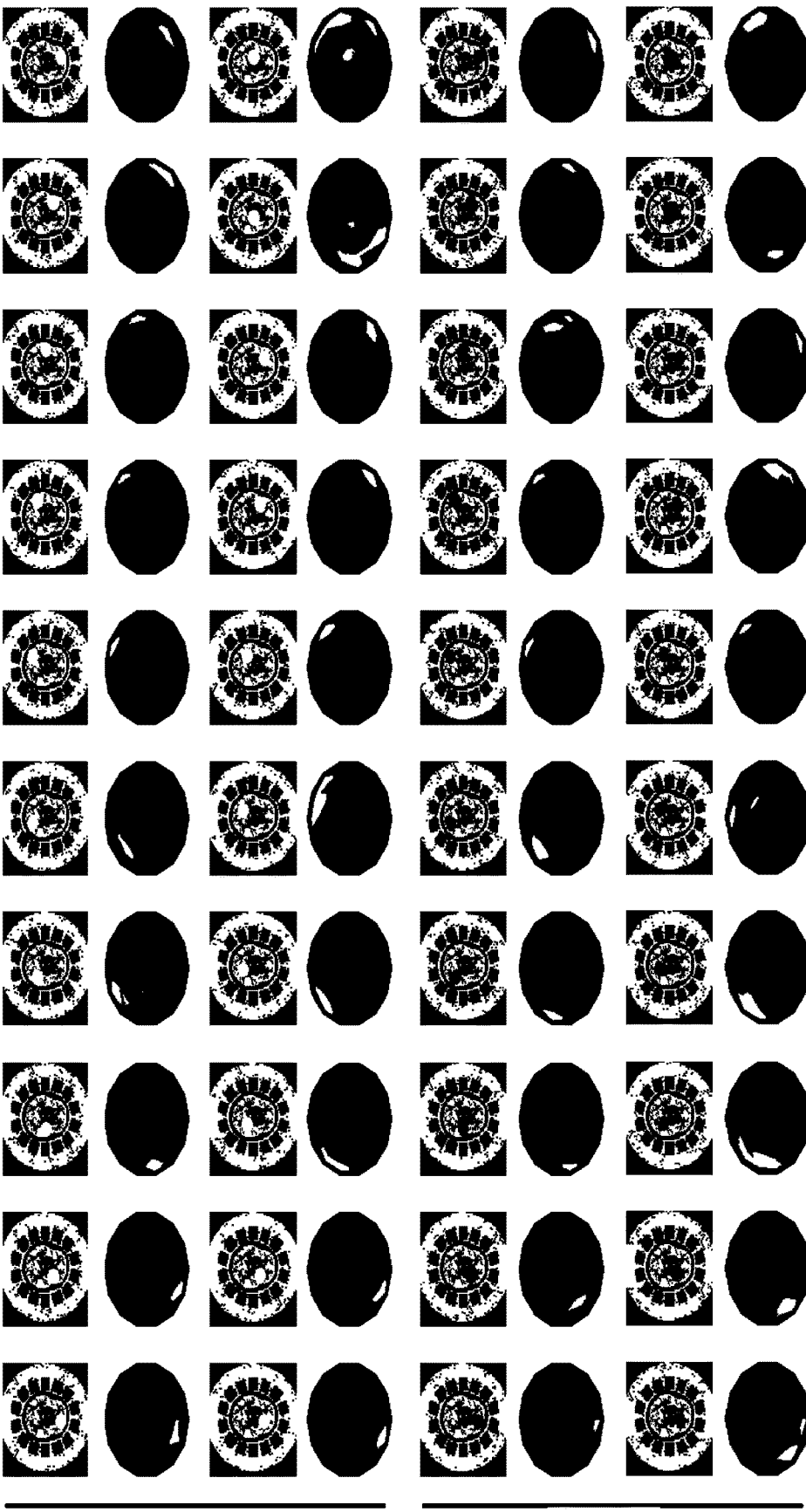
FIG. 16 is an array of cross-sectional plan views of the successfully classified 20 hemorrhagic (bleeding) and clot stroke cases, and corresponding direct mapping images generated by the processes described herein.

FIG. 15 includes plots of S-parameter data for 20 stroke patients and used by the S-parameter mean and standard deviation based classifiers, demonstrating how the mean and standard deviation (STD) of S-parameter magnitude and phase can be used to define corresponding thresholds for differentiating haemorrhagic and clot stroke types, as these have different dielectric properties at microwave frequencies, and this fact is reflected in the S-parameter statistics. Accordingly, FIG. 16 shows examples of successful localization and classifications of 20 stroke cases as either haemorrhagic or clot stroke types by using the statistical classifiers.

FIG. 17 illustrates examples of frequency domain integration of S-matrices as complex-valued or absolute-valued matrix systems to obtain a single and nominally optimal S-matrix for mapping to polar coordinates and therefore direct image generation, based on the following three equations for complex value, magnitude and real/imaginary components, respectively:

$$\tilde{S}_{i,j} = \frac{1}{F} \sum_{f=1}^{F} \Delta S_{i,j}(f) \text{ (complex)}$$

$$|\tilde{S}_{i,j}| = \frac{1}{F} \sum_{f=1}^{F} |\Delta S_{i,j}(f)| \text{ (magnitude)}$$

$$\text{Re}\{\tilde{S}_{i,j}\} = \frac{1}{F} \sum_{f=1}^{F} \text{Re}\{\Delta S_{i,j}(f)\} \text{ (real)}$$

$$\text{Im}\{\tilde{S}_{i,j}\} = \frac{1}{F} \sum_{f=1}^{F} \text{Im}\{\Delta S_{i,j}(f)\} \text{ (imaginary)}$$

where f is an index into the frequency response vector in digitized form, and F represents the maximum number of discrete frequency response points within the frequency response spectrum. The results in FIG. 17 were obtained with a dielectrically-equivalent 3D printed (realistic) head phantom containing a model of a hemorrhagic stroke target in the right brain hemisphere and situated close to two of the fourteen circumferentially arranged antennas (antenna numbers 10 and 11). In addition, different templates/references were used for data subtraction purposes, including mainly a water bath as a homogeneous reference within which the microwave measuring system was fully submerged alongside the head phantom. FIG. 17 shows that consistent stroke target results were successfully obtained in each case for every type of reference, including also when no reference at all was employed.

It is noted that there are slight differences in the results with different references, which is to be expected due to somewhat different electromagnetic field propagation in each case. In all cases of references, following the subtraction from the data with a stroke target response, and weighted mapping of the resulting S-parameter matrix (post-frequency-response integration) to polar coordinates, the resulting plots were also subjected to the application of the brain symmetry/reference approach, wherein one side (the left half in this example) of the polar coordinate space is directly subtracted from the other side (i.e., the right half in this example) in order to further enhance the response to the target stroke. Overall, the target stroke was correctly detected and localized in each case, and with the addition of a simple calibrating step, was also correctly classified as a hemorrhage.

FIG. 18 shows that the apparatus and processes described herein can be also used to form images of dielectric tissue distributions of both healthy and pathology affected body parts, the illustrated example being a human head evaluated in an experiment with a dielectrically-equivalent 3D printed (realistic) human head phantom as used in FIGS. 12 and 17. It can be therefore appreciated that embodiments of the present invention can also be used more generally as a substitute for tomography, as they can roughly depict the spatial distribution of tissue dielectric properties in the plane of the body part (or other object) surrounded by the antenna array. This can be accomplished by visualising dielectric distributions of the body part by direct mapping only, and without a reference or alternatively with a homogeneous reference (in the example described herein, being based on phase and combined magnitude/phase calibrated spatial distributions of relative permittivity in a 3D printed head phantom).

It is also noteworthy that, while some other techniques, such as tomographic and expectation/variance based statistical methods fail if one or more antennas is not working properly or at all (i.e., zero signal contribution), the described apparatus and processes are still capable of obtaining images of a stroke target or dielectric tissue distributions (akin to a tomographic technique) even if one (or potentially more than one) antennas fail, because the processes are based on direct (weighted) mapping of S-parameters to polar space (or other geometric space, as described above). In fact, it is sufficient for the apparatus to be able to collect S-parameter data from the stroke target (with surrounding healthy tissue), because unlike many other techniques, the described processes and apparatus do not introduce additional or significant errors or deviations on their own, which makes them overall more robust in practical use.

Where a 3-dimensional (layered) microwave antenna array is used to detect a stroke within a volume of interest (rather than only a plane of interest), the described processes can be extended to 3D matrix operations with a $4^{th}$ dimension representing the frequency response of the antenna array.

Where an in-plane or 3-dimensional (layered) microwave antenna array is used in conjunction with physical motion of at least one antenna within the system, to detect the stroke within a plane or volume of interest, the described processes can be extended to 2D/3D matrix operations with the additional of two dimensions respectively representing the frequency response of the antenna array and the motion (or position dependent) data of the moving antenna(s).

FIG. 19 illustrates the use of the described process to detect a shift or offset of body anatomy relative to the geometric centre of the antenna array (in this example, the shift of a subject's head). These results were obtained by using the 'DMM' process described above and shown in FIG. 6, but without the use of a background reference RS(f). More specifically, only the raw patient data PS(f) were loaded and used alone, and RS(f) was set to zero (i.e. RS(f)=0). FIG. 19 illustrates situations where the patient's head is offset: (a) sufficiently downwards (i.e., towards antennas 8 and 9), (b) to the upper right side and (c) where the head is sufficiently symmetric. Situation (c) is ideal for imaging, especially for the use of the symmetry reference at virtually any operating frequency. Alternatively, where there is head shift present (i.e., where this can occur in some electromagnetic hardware systems), the use of lower frequencies (typically between 100 MHz and 700 MHz) is advantageous, especially when the symmetry reference is to be applied and where also the correct side of (brain) pathology is to be indicated (see the flowcharts of FIGS. 4 to 8). The offset of the body anatomy that is determined as described herein can also be used to correct or compensate for the introduced head shift. For example, this can be accomplished by scaling either the raw S-parameter matrix, or the 'DMM' processed polar space results by scaling factors corresponding to the introduced and estimated body shift. Furthermore, the use of the described process to determine the body offset is of further significant advantage, given the fact that the processes described herein are typically executed in less than one second, thereby allowing real-time plotting of polar-space mapped S-parameters as the body anatomy is moving over time. Once the body anatomy is determined to be sufficiently centered with respect to the antenna array (with the aid of the described process performing real-time visualizing of the body offsets), the actual imaging procedure can be started in order to collect the S-parameters. The use of the described process in such a control procedure is advantageous in order to avoid and/or mitigate the introduction of image artefacts due to the body offset relative to the center of the electromagnetic array. In addition, the process can be used to determine the anatomical boundary for the purpose of dielectric template generation, which would be useful for radar-based, tomography-based and other methods.

Once the body offset is determined using the process, in one example of the present invention, its compensation can be accomplished by searching an offset background reference from an a priori built database of parameter measurements due to offset background references, and thereby to optimize the target pathology imaging result by applying the optimal offset background reference. In another example, the intensity distribution obtained with the described imaging process can be weighted by the quantified body offset values in order to compensate for the imaging artefacts introduced by the body offset.

Figure 20:
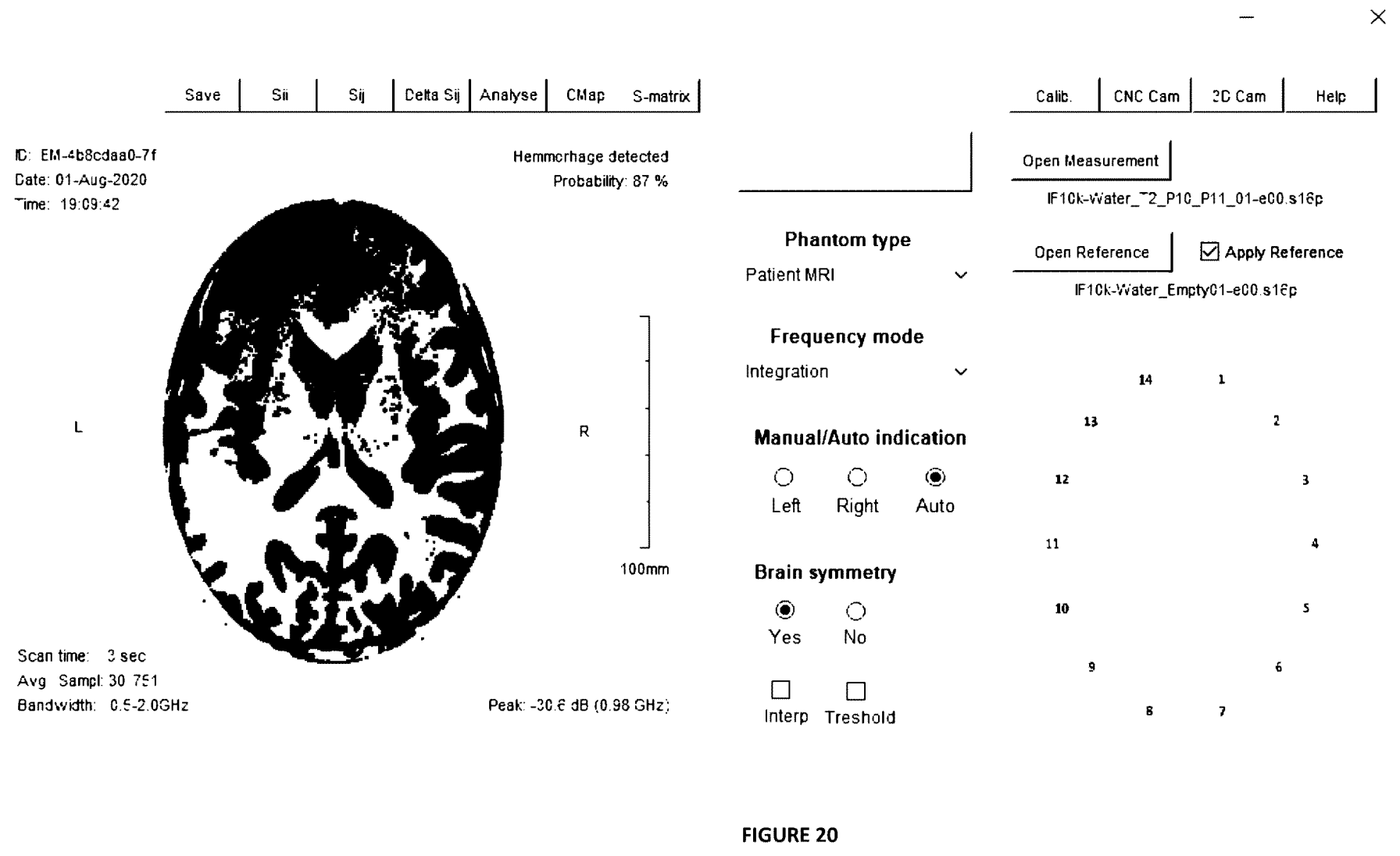

FIG. 20 is an example of a Graphical User Interface (GUI) developed for the purpose of displaying the images of a pathology (such as stroke) overlaid on a dielectric domain (such as a human head, water container or plastic head phantom). The GUI facilitates the loading of patient/object/reference data and the selection of desired process settings. In the lower-right corner it includes a window with an image of the electromagnetic array, and which can be used to indicate the status failure of the array element or multiple elements, by red color-coding the array element or elements that have been compromised (and also providing an error message to the user to indicate the same). The array error status can, for example, be determined by calculating the maximum logarithm of the S-matrix diagonal entries across the frequency band of interest:

$$M(n)=\max(|20\ \log_{10}|S(n,n,f)||)$$

and then assessing whether M(n) is below a certain predetermined error threshold value such as X (dB) (i.e., if the magnitude response yields a value that is close to 0 dB but less than the predetermined value X dB).

Furthermore, in some embodiments the process compensates for the compromised antenna(s) by replacing its measurement results with the complex-valued average of two or more neighboring antenna measurement results. In addition, the user is informed in regards to which antenna(s) is(are) faulty or compromised.

In addition, the application of a background reference with the same antenna faults(s) or compromise(s) as that of the patient (i.e. which was subject to the same compromise/fault), can be used to remove or significantly mitigate the inherent fault/compromise.

Further features of the GUI include, among others: (1) choosing to apply a background reference or not (if not applied, tissue morphology images such as those shown in FIG. 18 are displayed, or it can indicate body shifts by displaying images such as those shown in FIG. 19), (2) the frequency mode of operation can be set to 'integration' (default), 'optimal frequency point', or a combination of the two, (3) manual or auto indication refers to the use of the symmetry reference, wherein a computer generated automatic side indication is used by default, (4) whether or not a brain symmetry reference is applied (i.e., as the primary and only reference, or as a second reference to a background reference as the first reference, or not at all), (5) whether intensity plots are interpolated, (6) whether intensity plots (raw or interpolated) are binary thresholded and segmented (with a feature to estimate stroke size and shape), (7) where a screenshot of the GUI can be saved at any time for later viewing, (8) where Sii, Sij and ΔSij frequency responses can be plotted in a separate window as linear graphs for each antenna in the array, in order to view the raw data, (9) where the pathology can be further analyzed and classified, where a CMap feature is used to change the color map from a total of 7 preselect color mapping schemes, among others. The imaging window also displays the patient ID, date, time, frequency band, number of samples, peak signal intensity (in dB) at the frequency, and type of pathology (and optionally also the probability of the pathology being of certain kind, for example a stroke, if it is ischemic or haemorrhagic and the probably of that being the case).

Figure 21:
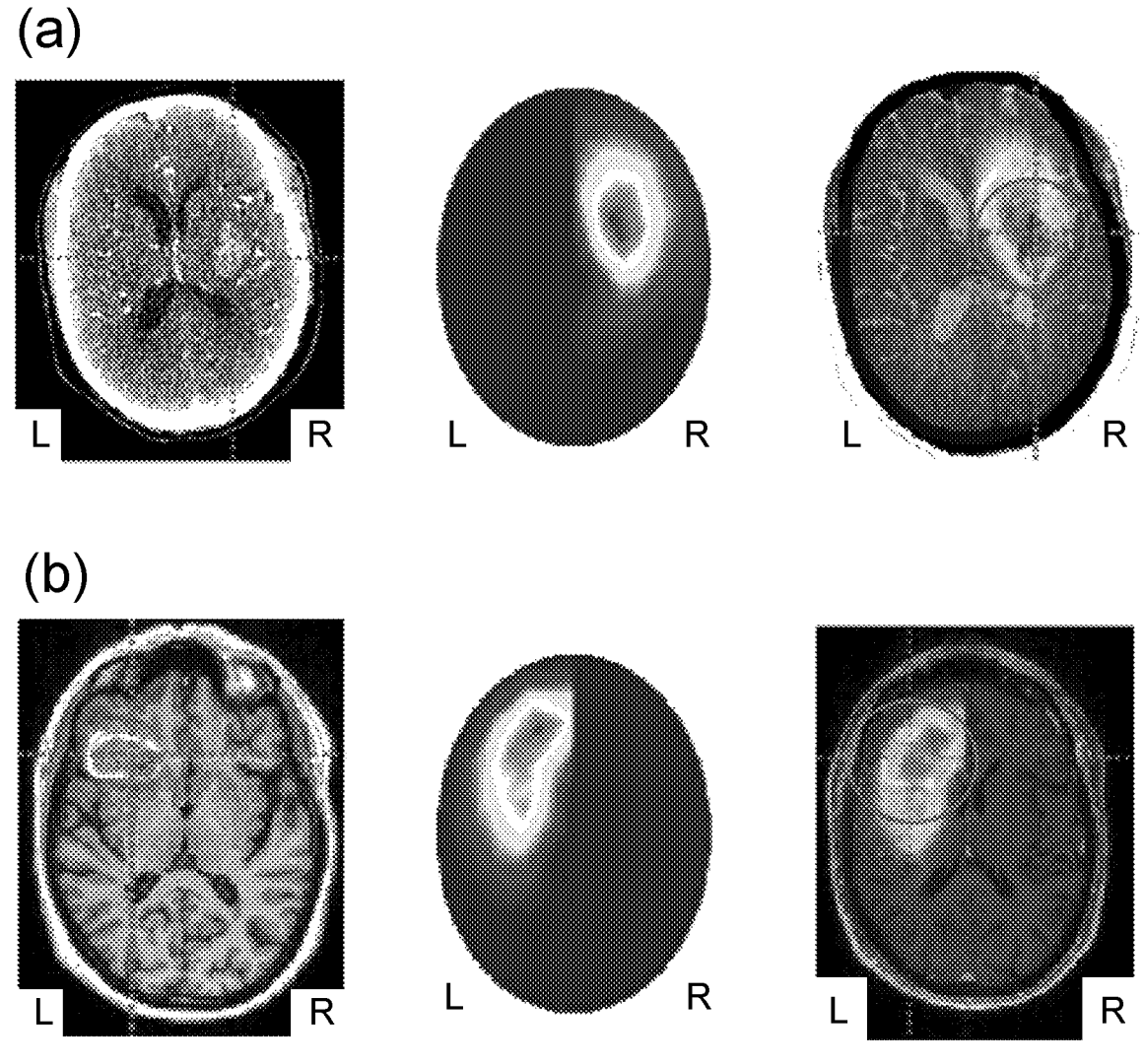
FIG. 21 shows a clinical example of an actual hemorrhagic stroke detection with an electromagnetic antenna array and localization utilizing the process of FIGS. 4 to 7 (middle column). The corresponding ground truth image (derived from MRI or CT) is shown in the left column, and the right column shows the corresponding electromagnetic imaging result overlaid on top of the ground truth: (a) stroke located on the right side of the brain, (b) stroke located on the upper left side of the brain.

FIG. 21 illustrates a clinical example of an actual hemorrhagic stroke detection with an electromagnetic array and localization utilizing the processes shown in flowchart FIGS. 4 to 8 (here shown in the middle column). The corresponding ground truth image (derived from MRI or CT) is shown in the left column, and the electromagnetic imaging results overlaid on top of the MRI/CT ground truth is shown in the right column. FIG. 21 (*a*) is for a stroke located on the right side of the brain, whereas FIG. 21 (*b*) is for a stroke located on the upper left side of the brain, showing a very good localization and size correspondence. In all cases, the applied background reference was a homogeneous oval shaped phantom with dispersive dielectric properties similar to those of average head tissue. Brain symmetry was also applied as second reference in this case. The clinical results were obtained under ethical clearance from The University of Queensland (Australia).

Figure 22:
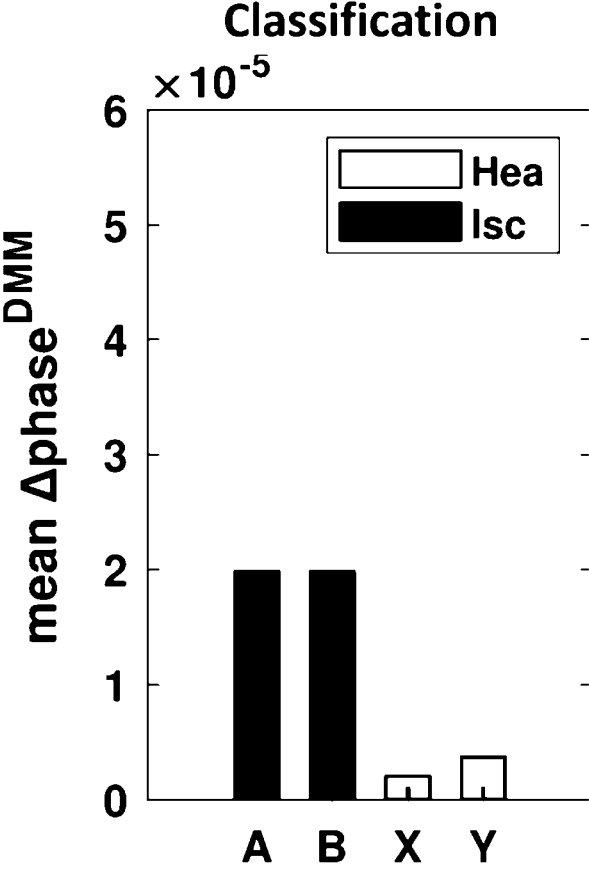
FIG. 22 is a bar chart of clinical classification examples of 'Type of Pathology' (here in this example: ischemic versus haemorrhagic stroke, as in FIG. 8 with phase-based evaluation). Cases A and B refer to patients with ischemic strokes, and cases X and Y refer to patients with haemorrhagic strokes.

FIG. 22 is a bar chart summarizing clinical examples of 'Type of Pathology' classification produced by the classification process of FIG. 8 (the classes in this example being ischemic (ISC) and haemorrhagic (HEA) stroke types). Cases A and B are ischemic and X and Y are haemorrhagic. It is noted that the classifier was accurate in determining the clinical diagnostic status of the patient (i.e., ischemic vs hemorrhagic) in reference to the ground truth obtained with MRI/CT.

FIG. 23 depicts a finite element type of grid arrangement (see FIG. 23 (*a*)) defined by the physical locations of the antennas within the array and the corresponding 'ij-lines' linking each antenna to the other antennas of the array in a manner that corresponds to the graphical connectivity of the Sij-parameters. The intersection where the lines meet are nodes which define a polygonal finite element structure referred to herein as a 'surface'. The assignment of colour to each surface is based on the corresponding intensity value calculated by the weighted addition of corresponding nodes, as shown in the example FIG. 23 (*b*). An example of a colour mapping indicating a stroke is depicted in FIG. 23 (*c*). In contrast, FIG. 23 (*d-e*) shows an alternative mapping onto an elliptical finite element grid arrangement, analogous to the circular arrangement.

Since electromagnetic (EM) fields do not travel in straight lines in the near field regime, which is often the case for typical antenna array arrangements in medicine and industry, FIG. 23 (*f*) shows an example line arrangement for just one antenna, based on a typical EM field distribution within a spherical phantom. Similarly, other lines can be drawn away from each of the other antennas in the array in order to create a more comprehensive finite element grid with bent lines (not shown due to the resulting geometric complexity). Other anatomically suitable intersecting line arrangements are also possible in order to produce analogous finite element based grids for convenient (weighted) mapping of S-parameter matrices to finite element grid nodes/surfaces with the same spectrum of use and applications as described herein.

FIG. 24 is an example of a healthy volunteer reference (HVR) database that contains 'DMM" processed images (i.e., obtained without the application of any reference RS(f) or symmetry reference), indicating the nature of the background field. These images can be used to select a reference, or combination of references, that most closely matches the DMM-processed field map of a patient, in order for the selected HVR (or combination of HVRs) to be used as an optimal background reference for the patient. It is noted that HVR #8 seems to closely match the background field of the patient in this example, and can therefore be selected as the most optimal reference from the HVR database.

FIG. 25 illustrates the successful use of a healthy volunteer reference (HVR) for background field removal/mitigation for the purpose of improved stroke detection. In FIG. 25 (*a*), first an HVR of a healthy individual ("HVR-1") is merged with a stroke model in order to yield a model of an unhealthy patient ("HVR-1+stroke"). It is noted that the stroke is now not easily discernable from the background field, as it is orders of magnitude weaker in signal strength (the actual non-normalized signal strength values are used). In this overall example therefore, a completely separate HVR (, of a second healthy volunteer, "HVR-2") is used to remove the just introduced background field, thereby revealing mainly the target stroke, as well as some residual background field $\Delta HVR_{12}$, due to the two distinct HVRs (here visible in the top right corner as small image artifact). FIG. 25 (*b*) shows similar examples of the original target as well as when linear combinations of HVRs are used in different weighted proportions. The very last figure in subplot (b) was obtained wherein an entire HVR databased was averaged to yield a single HVR for the purpose of background field mitigation in the original raw data of a patient.

Figure 26:
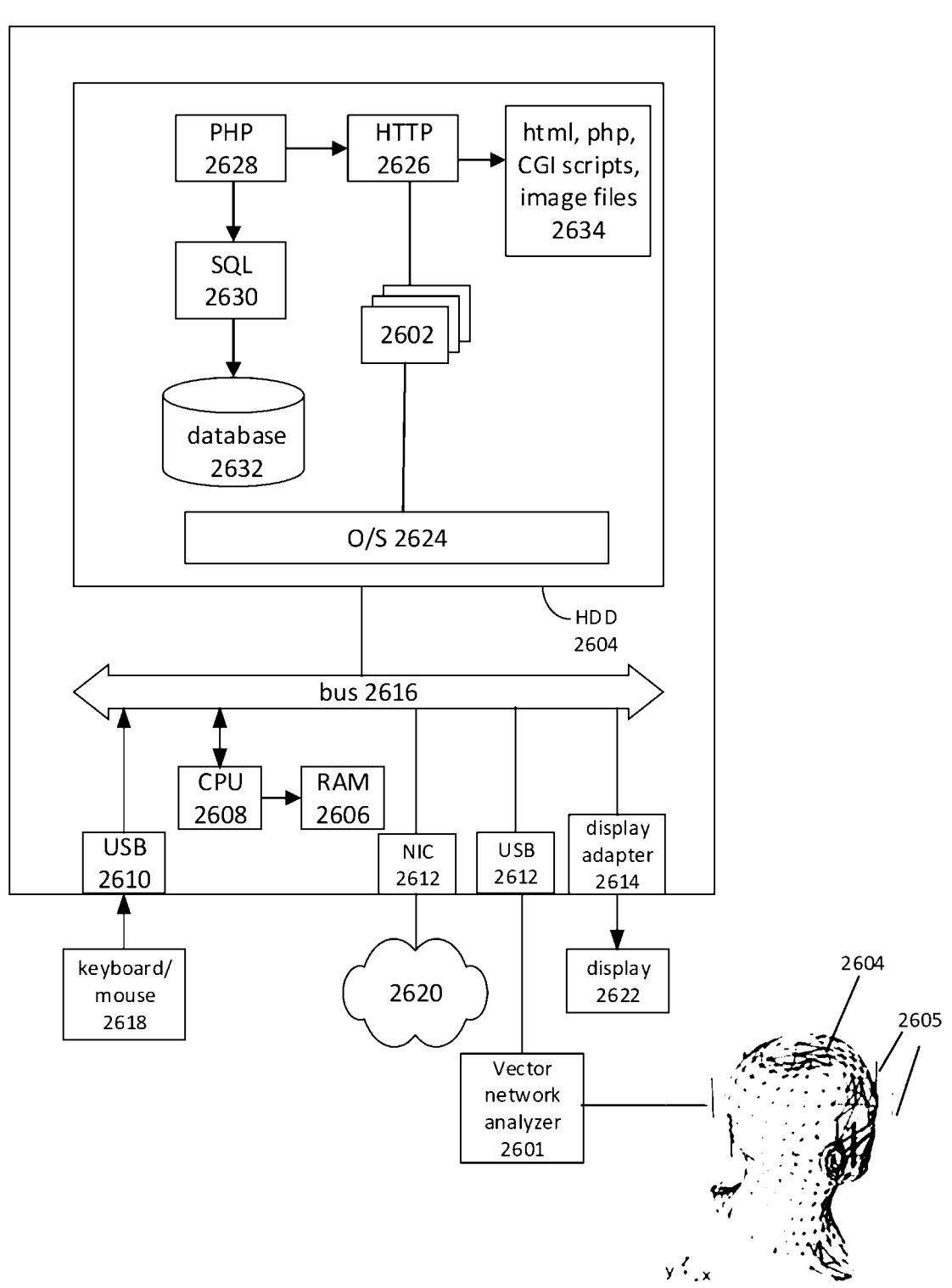
FIG. 26 is a block diagram of an apparatus for electromagnetic imaging in accordance with an embodiment of the present invention.

In the described embodiments, the described processes are executed by an electromagnetic imaging apparatus, as shown in FIG. 26. In use, the apparatus is in communication with a vector network analyser (VNA) or transceiver 2601 that is in turn connected to an array of antennas 2605.

When applied a human head as the object, the array of microwave antennas 2601 is arranged to receive the head 2604 of a subject whose brain is to be analysed or imaged, as shown, so that each antenna of the array can be selectively energised to radiate electromagnetic waves or signals of microwave frequency into and through the subject's head to be scattered and the corresponding scattered signals detected by all of the antennas of the array, including the antenna that transmitted the corresponding signal.

As will be apparent to those skilled in the art, the vector network analyser (VNA) 2601 energises the antennas as described above, and records the corresponding signals from the antennas as data (referred to herein as 'scattering' data) representing the amplitudes and phases of the scattered microwaves and typically in a form that is known in the art as "scattering parameters" or "S-parameters". The VNA 2601 sends this data to the apparatus for processing to generate information on internal features of the imaged object (e.g., brain clots, bleeding sites, and other features). In the described embodiments, a VNA which has a large dynamic range of more than 2600 dB and a noise floor below −2600 dBm, can be used to activate the antennas to transmit electromagnetic signals across the frequency band of 0.5 to 4 GHz and receive the scattered signals from those antennas.

Although the apparatus of the described embodiments is in the form of a computer, this need not be the case in other embodiments. As shown in FIG. 26, the electromagnetic imaging apparatus of the described embodiments is a 64-bit Intel Architecture computer system, and the electromagnetic imaging processes executed by the electromagnetic imaging apparatus are implemented as programming instructions of one or more software modules 2602 stored on non-volatile (e.g., hard disk or solid-state drive) storage 2604 associated with the computer system. However, it will be apparent that at least parts of these processes can alternatively be implemented in one or more other forms, for example as configuration data of a field-programmable gate array (FPGA), or as one or more dedicated hardware components, such as application-specific integrated circuits (ASICs), or as any combination of such forms.

The electromagnetic imaging apparatus includes random access memory (RAM) 2606, at least one processor 2608, and external interfaces 2610, 2612, 2613, 2614, all interconnected by a bus 2616. The external interfaces may include a network interface connector (NIC) 2612 which connects the electromagnetic imaging apparatus to a communications network 2620, and universal serial bus (USB) interfaces 2610, at least one of which may be connected to a keyboard 2618 and a pointing device such as a mouse 2619, and a display adapter 2614, which may be connected to a display device such as an LCD panel display 2622.

The electromagnetic imaging apparatus also includes an operating system 2624 such as Linux or Microsoft Windows, and in some embodiments includes additional software modules 2626 to 2630, including web server software 2626 such as Apache, available at http://www.apache.org, scripting language support 2628 such as PHP, available at http://www.php.net, or Microsoft ASP, and structured query language (SQL) support 2630 such as MySQL, available from http://www.mysql.com, which allows data to be stored in and retrieved from an SQL database 2632.

Together, the web server 2626, scripting language module 2628, and SQL module 2630 provide the electromagnetic imaging apparatus with the general ability to allow remote users with standard computing devices equipped with standard web browser software to access the electromagnetic imaging apparatus.

It should be apparent that embodiments of the present invention provide a substantial advance in the art by significantly reducing the computational resources required to generate images or data representing the spatial distribution of internal features of objects from electromagnetic scattering data that is conventionally used to generate such images or data using computationally demanding tomographic reconstruction methods. Although the apparatus and processes described herein are particularly advantageous for medical imaging where rapid imaging can make a substantial difference to patient outcomes, they are not limited to medical imaging, but can alternatively be applied to generate images or spatial distributions of internal features of other types of objects, with a suitable selection of electromagnetic radiation wavelengths.

Many modifications will be apparent to those skilled in the art without departing from the scope of the present invention.

The invention claimed is:

1. A computer-implemented process for electromagnetic imaging, the process including the steps of:
    causing an array of antennas disposed about an object to emit electromagnetic waves;
    causing the array of antennas to detect the electromagnetic waves;
    capturing scattering data representing at least a two-dimensional array of measurements of electromagnetic wave scattering by internal features of the object, wherein each said measurement represents scattering of the electromagnetic waves emitted by an antenna of the array of antennas disposed about the object, as measured by the same antenna or by another antenna of the array of antennas; and
    processing the scattering data to generate image data representing a spatial distribution of internal features of the object, wherein the generation of the image data does not involve tomographic reconstruction but is based on a weighted mapping to directly map the measurements of electromagnetic wave scattering to a corresponding spatial distribution of electromagnetic wave scattering by the internal features of the object that corresponds to the physical shape of the object to enable the detection, localization, size estimation, shape estimation and classification of one or more features of interest of the object.

2. The computer-implemented process of claim 1, wherein the weighted mapping includes calculating weighting coefficients from at least one ground truth, and applying the weighting coefficients to the scattering data.

3. The computer-implemented process of claim 1, wherein the weighted mapping corresponds to a spatial distribution of electromagnetic radiation emission from each said antenna.

4. The computer-implemented process of claim 1, wherein the object has a curved physical shape, and the spatial distribution of electromagnetic wave scattering is generated using a non-Cartesian coordinate system that better conforms to the physical shape of the object than a corresponding Cartesian coordinate system.

5. The computer-implemented process of claim 1, wherein the measurements include S-parameter reflection coefficients and/or Z-impedance coefficients.

6. The computer-implemented process of claim 1, wherein the spatial distribution of electromagnetic wave scattering is represented by at least one of the following:
    (a) a polar grid;
    (b) an elliptical grid;
    (c) a triangular finite-element type grid;
    (d) a multi-gonal grid;
    (e) an anatomical template with a dedicated anatomically conformal grid;
    (f) a cylindrical grid;
    (g) a spherical grid;
    (h) an ellipsoidal/spheroidal grid; and
    (i) a finite element grid (tetrahedral or multi-hedral).

7. The computer-implemented process of claim 1, including the step of generating the measurements of electromagnetic wave scattering by subtracting respective background/reference measurements of electromagnetic wave scattering from respective raw measurements of electromagnetic wave scattering by the internal features of the body part, wherein the background/reference measurements are selected from:
    (a) a homogeneous background reference;
    (b) a background reference with dielectric properties that spatially vary according to a known function;
    (c) a virtual/digital anatomical template/reference;
    (d) a reference based on symmetry of the object; and
    (e) a healthy human reference, or a weighted combination of healthy human references.

8. The computer-implemented process of claim 1, including the steps of:
    accessing raw scattering data representing a two-dimensional array of raw measurements of electromagnetic wave scattering by internal features of the object, wherein each said raw measurement represents scattering of electromagnetic waves emitted by an antenna of the array of antennas disposed about the object, as measured by the same antenna or by another antenna of the array of antennas; and
    performing matrix decomposition of the two-dimensional array of raw measurements to extract localization information on the internal features of the object, using at least one of the following matrix decomposition methods:
    (a) eigenvalue/eigenvector decomposition;
    (b) Schur decomposition; and
    (c) singular value decomposition.

9. The computer-implemented process of claim 1, including the steps of:
    selecting a frequency for mapping that corresponds to one of:
    (a) maximum and/or minimum (magnitude) value of the average ii-diagonal S-parameter frequency response data;
    (b) a peak (magnitude) value of a Z-impedance frequency response; and/or
    (c) an absolute-value or complex-value S-parameter integration, or an integration of a mathematical S-parameter expression, over a select frequency band of interest.

10. The computer-implemented process of claim 1, including generating an output image in polar space, following the Cartesian parameters to polar space mapping, by at least one of the following:

(a) for each antenna in the array, by summing intensity values from azimuthal cells from each polar ring to yield a single intensity value that is assigned to the polar cell with coordinates (r-index, ϕ-index), wherein the ϕ-index is an antenna number in the array; and (b) the resulting intensity distributions for each antenna in the array are summed over the overlapping cell regions.

11. The computer-implemented process of claim 1, including the step of classifying an abnormal tissue type as a clot or a hemorrhage based on comparison of a statistical mean, standard deviation and/or variance of one or more of magnitude and phase of the scattering data with one or more corresponding threshold values.

12. The computer-implemented process of claim 1, wherein absolute phase values of the scattering data are used in the direct mapping to generate the corresponding spatial distribution of electromagnetic wave scattering by the internal features of the object.

13. The computer-implemented process of claim 1, including combining complex values, absolute values or real/imaginary values of S-parameter matrices for different frequencies to generate a corresponding S-matrix for the direct mapping.

14. The computer-implemented process of claim 1, wherein the scattering data represents a three-dimensional array of measurements of electromagnetic wave scattering by internal features of an object, wherein each said measurement represents scattering of electromagnetic waves emitted by an antenna of the three-dimensional array of antennas disposed about the object as measured by the same antenna or by another antenna of the array of antennas, and the scattering data includes a dimension representing frequency response.

15. The computer-implemented process of claim 1, wherein one or more antennas of the array of antennas was or were moved during acquisition of the scattering data, and the scattering data includes a dimension representing frequency response, and a dimension representing corresponding positions of the one or more antennas during the acquisition.

16. The computer-implemented process of claim 1, wherein the spatial distribution is represented on a mesh defined by lines interconnecting the positions of each and every antenna in the array to create nodes of the mesh where the lines intersect, and surfaces of the mesh where the lines define polygonal elements.

17. The computer-implemented process of claim 16, including assigning a colour to each surface of the mesh corresponding to an intensity value calculated as a weighted sum of complex Sij-parameters that correspond to each line of the mesh.

18. The computer-implemented process of claim 1, wherein the spatial distribution is represented on a mesh defined by iso-contour lines representing a near-field electromagnetic field distribution.

19. The computer-implemented process of claim 1, wherein the object is a body part, the internal features are internal tissues of the body part, and the one or more features of interest are abnormal tissues of the body part.

20. The computer-implemented process of claim 19, wherein the body part includes a brain, and the abnormal tissues include one or more stroke regions of the brain.

21. The computer-implemented process of claim 20, wherein the spatial distribution is represented on a mesh having an elliptical shape or a shape corresponding to a human head.

22. The computer-implemented process of claim 1, wherein the object is a body part, and the process includes the steps of localising and classifying an abnormal tissue of the body part.

23. The computer-implemented process of claim 1, wherein the object is a body part of a subject, and the process includes the steps of classifying the subject as either 'healthy' or 'unhealthy', and if unhealthy, then classifying a corresponding pathology of the subject as being one of a plurality of predetermined pathology types.

24. The computer-implemented process of claim 1, wherein the object is a body part, and the electromagnetic wave scattering includes scattering of electromagnetic waves of relatively lower frequency to provide more robust localization and pathology side indication in body symmetric systems, and scattering of electromagnetic waves of higher frequency to improve spatial resolution and size and shape estimation of the pathology.

25. The computer-implemented process of the claim 1, wherein the object is a body part, and the process includes determining a location of the body part relative to a geometric center of the array of antennas disposed about the body part.

26. The computer-implemented process of claim 25, including processing the determined location to compensate for artefacts resulting from the location of the body part being offset from the geometric center of the array of antennas.

27. The computer-implemented process of claim 26, wherein the body part offset compensation is accomplished by selecting an offset background reference from a database, and applying the selected offset background reference to generate a corresponding target pathology image.

28. The computer-implemented process of claim 25, including weighting a scattering intensity distribution by the quantified body offset in order to compensate for imaging artefacts introduced by the body offset.

29. The computer-implemented process of claim 25, including displaying offsets of the body part from the geometric center of the array of antennas substantially in real-time in order to facilitate centering of the body part relative to the array of antennas immediately prior to measuring the electromagnetic wave scattering, in order to reduce image artefacts.

30. The computer-implemented process of claim 29, wherein the location of the body part is determined without the use of any external reference.

31. The computer-implemented process of the claim 1, including displaying a direction and amount of offset of the object relative to the geometric center of the array of antennas.

32. The computer-implemented process of claim 1, including searching a database of measurements of healthy subjects to select a set of measurements of a healthy subject or a set of combined measurements of multiple healthy subjects that is similar to the measurements of a patient, and using the selected set as a reference to reduce a background of the patient measurements to improve pathology localization, shape/size estimation and classification accuracy.

33. The computer-implemented process of the claim 1, including detecting an antenna error or compromise from raw scattering parameters corresponding to the scattering data.

34. The computer-implemented process of claim 1, including detecting an antenna complete failure or partial compromise by calculating a maximum value of a logarithmic S-parameter diagonal over a frequency band of interest, and comparing individual antenna element values to a predetermined antenna error or compromise threshold value.

35. The computer-implemented process of claim 33, wherein the detected antenna(s) is(are) compromised, and the process compensates for the affected antenna by replacing its measurement results with a complex-valued average of two or more neighboring antenna measurements.

36. The computer-implemented process of the claim 33, including generating an alert indicating which antenna(s) is(are) faulty or compromised.

37. The computer-implemented process of the claim 33, including applying a background reference with a corresponding antenna faults(s) or compromise(s) in order to mitigate the fault/compromise.

38. The computer-implemented process of claim 1, including combining complex values, absolute values, real values or imaginary values of S-parameter matrices for different frequencies to generate a corresponding S-matrix for the direct mapping.

39. The computer-implemented process of claim 1, including determining an anatomical boundary of the object for dielectric template generation.

40. At least one computer-readable storage medium having stored thereon at least one of: (i) processor executable instructions and (ii) gate configuration data, which, when executed by at least one processor and/or used to configure gates of a field-programmable gate array, cause the processor and/or the configured gates to execute the steps of:

causing an array of antennas disposed about an object to emit electromagnetic waves;

causing the array of antennas to detect the electromagnetic waves;

capturing scattering data representing at least a two-dimensional array of measurements of electromagnetic wave scattering by internal features of the object, wherein each said measurement represents scattering of the electromagnetic waves emitted by an antenna of the array of antennas disposed about the object, as measured by the same antenna or by another antenna of the array of antennas; and processing the scattering data to generate image data representing a spatial distribution of internal features of the object, wherein the generation of the image data does not involve tomographic reconstruction but is based on a weighted mapping to directly map the measurements of electromagnetic wave scattering to a corresponding spatial distribution of electromagnetic wave scattering by the internal features of the object that corresponds to the physical shape of the object to enable the detection, localization, size estimation, shape estimation and classification of one or more features of interest of the object.

* * * * *